US012698508B2

(12) United States Patent
Prins et al.

(10) Patent No.: US 12,698,508 B2
(45) Date of Patent: Aug. 4, 2026

(54) GEMINIVIRUS RESISTANT PLANTS

(71) Applicant: Keygene N.V., Wageningen (NL)

(72) Inventors: Marinus Willem Prins, Wageningen (NL); Leonora Johanna Gertruda Van Enckevort, Wageningen (NL); Hans Peter Versluis, Wageningen (NL)

(73) Assignee: Keygene N.V., Wageningen (NL)

( * ) Notice: Subject to any disclaimer, the term of this patent is extended or adjusted under 35 U.S.C. 154(b) by 0 days.

(21) Appl. No.: 16/906,821

(22) Filed: Jun. 19, 2020

(65) Prior Publication Data

US 2020/0392530 A1     Dec. 17, 2020

Related U.S. Application Data

(63) Continuation of application No. PCT/EP2018/086688, filed on Dec. 21, 2018.

(30) Foreign Application Priority Data

Dec. 21, 2017    (EP) ..................................... 17209603

(51) Int. Cl.
*C12N 15/82*        (2006.01)
*C12N 15/01*        (2006.01)
(52) U.S. Cl.
CPC ......... *C12N 15/8283* (2013.01); *C12N 15/01* (2013.01)
(58) Field of Classification Search
None
See application file for complete search history.

(56) References Cited

FOREIGN PATENT DOCUMENTS

WO     WO-2014/045206 A1     3/2014

OTHER PUBLICATIONS

Sequence Accession BBE36056, May 22, 2014. Sequence alignment attached at the end of the office action. (Year: 2014).*
Sequence Accession BBE36057, May 22, 2014. Sequence alignment attached at the end of the office action. (Year: 2014).*

GenBank Accession No. XP_016572281 (submitted on May 5, 2016).*
Koeda et al, Theor Appl. Genetics (2021) 134:2947-2964.*
Hutton et al., "Recent progress in TYLCV resistance breeding, and implications for tomato varieties of the future," University of Florida, IFAS, 2015.
Lapidot et al, A Novel Route Controlling Begomovirus Resistance by the Messenger RNA Surveillance Factor Pelota, PLoS Genetics (2015) 11(10):e1005538.
Levin et al., "Cloning and Analysis of the Tomato yellow leaf curl virus Resistance Gene Ty-5," Institute of Plant Sciences, 2013.
Database UniProt [Online] May 10, 2017, "RecName: Full=Protein pelota homolog {ECO:0000256|RuleBase:RU362019}; EC=3.1.-.-{ECO:0000256|RuleBase:RU362019};", XP002779834, retrieved from EBI accession No. Uniprot: A0A1U8GLY1, Database accession No. A0A1U8GLY1.
Database UniProt [Online] Oct. 1, 2014, "SubName: Full=Uncharacterized protein {ECO:0000313 |EMBL:CD099955.1}", XP002779833, retrieved from EBI accession No. UNIPROT:A0A068TUH6, Database accession No. A0A068TUH6.
Database UniProt [Online] May 10, 2017, "SubName: Full=Uncharacterized protein {ECO:0000313|EMBL:CD099955.1};" XP002788599, retrieved from EBI accession No. Uniprot: A0A068TUH6, Database accession No. A0A068TUH6 sequence.
International Search Report mailed Feb. 28, 2019 received in corresponding International Application No. PCT/EP2018/086688 (3 pages).
Hutton, et al., "Recent Progress in TYLCV resistance breeding, and implications for tomato varieties of the future." University of Florida, IFAS, 2015, accessed via hypertexttransferprotocol://swfrec.ifas.ufl.edu/docs/pdf/veg-hort/tomato-institute/presentations/ti2015/ti2015_Hutton.pdf.

* cited by examiner

*Primary Examiner* — Mykola V. Kovalenko
(74) *Attorney, Agent, or Firm* — Foley & Lardner LLP

(57)        ABSTRACT

A dicot plant cell, plant tissue or plant having a reduced expression of a wild type protein having at least 75% sequence identity with SEQ ID NO. 1 is disclosed. Also disclosed is a plant cell, plant tissue or plant comprising a modified protein and/or a truncated protein having at least about 75% sequence identity when calculated over the positions corresponding to positions 1-66 and positions 78-308 of SEQ ID NO: 1. The modified protein increases the resistance to Geminiviridae. Nucleic acid constructs encoding the modified or truncated protein are also provided. Lastly, methods for generating a plant cell, plant tissue or plant comprising the modified protein that increases the resistance to Geminiviridae are disclosed.

6 Claims, 2 Drawing Sheets

Specification includes a Sequence Listing.

- ▨ Col0_Control
- ▨ Col0_BCTV
- ◩ T-DNA insertion line Control
- ▨ T-DNA insertion line_BCTV

- ▨ Col0_Control
- ◻ Col0_BCTV
- ◩ T-DNA insertion line Control
- ▨ T-DNA insertion line_BCTV
- ◻ T-DNA insertion line_dTP_Manes_BCTV
- ▨ T-DNA insertion line_dTP_Zucchini_BCTV
- ▧ T-DNA insertion line_dTP_Pepper_BCTV
- ▤ T-DNA insertion line_dTP_Arabidopsis_BCTV
- ▨ T-DNA insertion line_dTP_G.hirsutum_BCTV

GEMINIVIRUS RESISTANT PLANTS

CROSS-REFERENCE TO RELATED APPLICATIONS

This application is a continuation of International Application No. PCT/EP2018/086688 filed Dec. 21, 2018, which claims the benefit of and priority to European Application No. 17209603.4 filed Dec. 21, 2017, both of which are hereby incorporated by reference herein in their entireties.

SEQUENCE LISTING

The instant application contains a Sequence Listing which is being submitted in ASCII format via EFS-WEB and is hereby incorporated by reference in its entirety. Said ASCII copy, created on Jun. 15, 2021, is named 085342-3600SequenceListing.txt and is 69 kb.

FIELD OF THE INVENTION

The present invention relates to the field of plant breeding and molecular biology. The invention relates to plants which harbor mutations which confer resistance to Geminiviridae.

BACKGROUND

Insect-transmitted viruses cause some of the most damaging and economically important diseases of crop plants. The geminiviruses, a group of single-stranded DNA viruses with unique twined icosahedral virus particles, are responsible for many of these diseases.

Geminiviruses comprise a biologically and genetically diverse family (Geminiviridae) of viruses that share the following characteristics: a twinned quasi-icosahedral virus particle (virion) that measures ~18×30 nanometers and a small circular single-stranded DNA genome of ~2.9-5.2 kilobases (kb). Based upon genome structure, phylogenetic relationships, insect vector and host range, seven genera have been recognized: *Begomovirus, Mastrevirus, Curtovirus, Topocuvirus, Becurtovirus, Turncurtovirus* and *Eragrovirus*. Geminiviruses often occur in disease complexes, and individual plants can be infected with multiple viruses. Geminivirus genomes can undergo high rates of mutation, recombination and re-assortment to increase viral diversity. Their genomes consist of one (monopartite) or two (bipartite) DNA components that encode 5-7 proteins involved in viral replication, movement, transmission and pathogenesis In nature, Geminiviruses are transmitted by phloem-feeding insects, including various species of leafhoppers, treehoppers and whiteflies. Plants infected with Geminiviruses show a wide range of symptoms including stunting; distorted growth; and leaf streaking and striations in monocotyledonous plants and leaf crumpling, curling, distortion, golden-light green-yellow mosaic/mottle, interveinal yellowing, yellow spots, and vein swelling, purpling, and yellowing in dicotyledonous plants.

Of particular importance are the geminiviruses transmitted by whiteflies (*Bemisia tabaci*), which are in the genus *Begomovirus*. This is the largest genus of plant viruses (in terms of numbers of species), and some are responsible for many devastating diseases in vegetable and fiber crops throughout the world. Management of *Begomoviruses* is difficult because its whitefly vector populations can reach enormous numbers. Therefore, breeding *Begomoviruses* resistant crops provides an attractive, environmentally sound, strategy to reduce yield losses inflicted by the virus.

*Begomoviruses* can either have a bipartite genome (mostly of South American origin), with the A component encoding five or six proteins and the B component encoding two proteins, each component being 2.5-2.8 kb in size, or a monopartite genome encoding six proteins with or without satellite DNA components.

An example of a *Begomovirus* is the tomato yellow leaf curl virus (TYLCV) which is one of the most devastating viruses of cultivated tomatoes. It has been shown previously in the art that silencing the expression of the tomato Pelo gene renders the transgenic plants resistant to TYLCV (WO2014/045206; Lapidot et al, A Novel Route Controlling *Begomovirus* Resistance by the Messenger RNA Surveillance Factor Pelota, PLOS Genetics (2015) 11 (10): e1005538). Silencing the expression of the Pelo gene in tomato however also results in a reduction in total yield and a reduction in fruit size (Lapidot M et al, supra). In addition, silencing of the tomato Pelo gene may provide resistance against a monopartite member of the family Geminiviridae but does not provide any resistance against bipartite Geminiviridae family members. Hence, the use of silencing the Pelo gene in tomato appears to be limited.

Geminiviruses infections have also emerged in pepper, which has caused severe problems in pepper cultivation in Asia. Outbreaks of Pepper Yellow Leaf Curl Virus (PYLCV) (De Barro et al. (2008) *A virus and its vector, pepper yellow leaf curl virus and Bemisia tabaci, two new invaders of Indonesia*. Biological Invasions Vol 10 (4), p 411-433) and Chilli Leaf Curl Virus (ChiLCV) have devastated crops while in Mexico and the Southern US pepper mixed infections with huasteco yellow vein virus (PHYVV) and Pepper Golden mosaic virus (PepGMV) (Renteria-Canett et al., 2011) have emerged. To date, no suitable resistance sources have been identified in pepper germplasm.

Hence, Geminiviruses have emerged as devastating pathogens, particularly in the tropics and subtropics, causing huge economic losses and threatening crop production. Epidemics caused by re-emerging and newly emerging Geminiviruses are becoming frequent even in regions that were earlier free from these viruses. Spreading of the viruses is expected to grow further due to the global movement of plant material and the dissemination of the whitefly vector. Hence, there is a strong need in the art for plant variants which exhibit resistance against Geminiviruses. In particular, there is a strong need for pepper plants that are resistant against Geminivirus infections. In addition, there is a need for an effective method of producing such resistant plants.

SUMMARY OF THE INVENTION

In a first aspect, the invention pertains to a plant cell, plant tissue or plant having a reduced expression of a wild type protein, wherein the wild type protein has at least about 75% sequence identity with SEQ ID NO: 1 over its full length, and wherein preferably the wild-type protein is not expressed in the plant cell, plant tissue or plant.

Preferably, the plant cell, plant tissue or plant has an increased resistance to at least one bipartite member of the Geminiviridae family as compared to an otherwise identical plant cell, plant tissue or plant not having a reduced expression of said wild type protein.

Preferably, the plant cell, plant tissue or plant has an increased resistance to at least one bipartite member and at least one monopartite member of the Geminiviridae family.

Preferably, the plant cell, plant tissue or plant as defined herein further expresses a modified protein that has at least about 75% sequence identity when calculated over the positions corresponding to positions 1-66 and positions 78-308 of SEQ ID NO: 1 and wherein a) the modified protein comprises a modification of one or more amino acid residues corresponding to positions 67-77 of SEQ ID NO: 1; or b) the modified protein is a truncated protein having a deletion corresponding to positions 309-378 of SEQ ID NO: 1, wherein expression of the modified protein increases resistance to Geminiviridae as compared to an otherwise identical plant cell, plant tissue or plant expressing the protein without the modification or without the truncation.

Preferably, the germination potential remains similar to the germination potential of an otherwise identical plant cell, plant tissue or plant expressing the protein without the modification.

In a preferred embodiment, the modification is a deletion of at least one, two or three amino acid residues, wherein preferably the modification is the deletion of at least one amino acid residue at position 71, 72 or 73 of SEQ ID NO: 1.

Preferably, the modification is a deletion of the amino acid residues at positions 71, 72 and 73 of SEQ ID NO: 1.

Preferably, the modified protein comprising a modification of one or more amino acid residues corresponding to positions 67-77 of SEQ ID NO: 1 has at least 95% sequence identity when calculated over the positions corresponding to positions 1-66 and positions 78-378 of SEQ ID NO: 1.

In a further embodiment, the modified protein comprising a modification of one or more amino acid residues corresponding to positions 67-77 of SEQ ID NO: 1 is encoded by a nucleic acid comprising a sequence having at least 75% sequence identity with SEQ ID NO: 4.

Preferably, the Geminivirus is of the genus of the *Begomovirus*.

In a preferred embodiment, the plant cell, plant tissue or plant as defined herein is a dicotyledonous plant, preferably selected from the group consisting of *Capsicum, Solanum lycopersicum, Manihot esculenta, Gossypium*, Cucurbitaceae (e.g. *Cucurbita pepo, Cucurbita moschata, Cucumis melo* and *Cucumis sativus*), *Solanum melongena, Abelmoschus esculentus* and Fabaceae.

Preferably, the plant is a *Capsicum*, preferably a *Capsicum annuum* and wherein the modification increases the resistance to Pepper Yellow Leaf Curl Indonesia Virus and/or Pepper Leaf Curl Virus.

In a second aspect, the invention relates to a modified protein having at least 75% sequence identity with SEQ ID NO: 1 over its full length, and wherein i) the modified protein comprises a modification of one or more amino acid residues corresponding to positions 67-77 of SEQ ID NO: 1, and wherein preferably the protein has the sequence of SEQ ID NO: 3; or ii) the modified protein is a truncated protein having a deletion corresponding to positions 309-378 of SEQ ID NO: 1, and wherein preferably the protein has the sequence of SEQ ID NO: 5.

In a third aspect, the invention concerns a nucleic acid comprising a sequence encoding the protein as defined herein.

In a fourth aspect, the invention concerns a nucleic acid construct comprising the nucleic acid as defined herein, wherein the nucleic acid is preferably operably linked to a promoter for expression in a plant cell.

In a fifth aspect, the invention pertains to a method for generating a plant cell, plant tissue or plant having increased resistance to Geminiviridae comprising the steps of i) providing a plant cell, plant tissue or plant;

ii) reducing the expression of a wild type protein, wherein the protein has at least about 75% sequence identity with SEQ ID NO: 1 over its full length, wherein preferably the wild-type protein is not expressed;

iii) selecting a plant cell, plant tissue or plant having reduced expression of the wild-type protein, preferably wherein the wild type protein is not expressed; and iv) regenerating the selected plant.

Preferably, step ii) is performed by modifying the gene encoding the wild-type protein resulting in a gene encoding a modified protein that comprises a modification of one or more amino acid residues corresponding to positions 67-77 of SEQ ID NO: 1; or in a gene encoding a modified protein is a truncated protein having a deletion corresponding to positions 309-378 of SEQ ID NO: 1.

In a preferred method of the invention the plant is a dicot, preferably selected from the group consisting the group consisting of *Capsicum, Solanum lycopersicum, Manihot esculenta, Gossypium*, Cucurbitaceae, *Solanum melongena, Abelmoschus esculentus* and Fabaceae.

In a further preferred method, the Geminiviridae is of the genus of the *Begomovirus*.

In a sixth aspect, the invention relates to a plant obtainable by the method of the invention as defined herein.

In a further aspect, the invention pertains to a method for increasing the resistance to at least a bipartite member of the Geminiviridae family in a plant cell, plant tissue or plant, wherein the method comprises the steps of:

i) providing a plant cell, plant tissue or plant;

ii) reducing the expression of a wild type protein, wherein the protein has at least about 75% sequence identity with SEQ ID NO: 1 over its full length, wherein preferably the wild-type protein is not expressed; and iii) optionally screening the plant cell, plant tissue or plant for increased resistance to at least a bipartite member of Geminiviridae.

Definitions

Various terms relating to the methods, compositions, uses and other aspects of the present invention are used throughout the specification and claims. Such terms are to be given their ordinary meaning in the art to which the invention pertains, unless otherwise indicated. Other specifically defined terms are to be construed in a manner consistent with the definition provided herein. Although any methods and materials similar or equivalent to those described herein can be used in the practice for testing of the present invention, the preferred materials and methods are described herein.

Methods of carrying out the conventional techniques used in methods of the invention will be evident to the skilled worker. The practice of conventional techniques in molecular biology, biochemistry, computational chemistry, cell culture, recombinant DNA, bioinformatics, genomics, sequencing and related fields are well-known to those of skill in the art and are discussed, for example, in the following literature references: Sambrook et al., Molecular Cloning. A Laboratory Manual, 2nd Edition, Cold Spring Harbor Laboratory Press, Cold Spring Harbor, N. Y., 1989; Ausubel et al., Current Protocols in Molecular Biology, John Wiley & Sons, New York, 1987 and periodic updates; and the series Methods in Enzymology, Academic Press, San Diego.

The singular terms "a," "an," and "the" include plural referents unless the context clearly dictates otherwise. Thus, for example, reference to "a cell" includes a combination of two or more cells, and the like. The indefinite article "a" or "an" thus usually means "at least one".

The term "and/or" refers to a situation wherein one or more of the stated cases may occur, alone or in combination with at least one of the stated cases, up to with all of the stated cases.

As used herein, the term "about" is used to describe and account for small variations. For example, the term can refer to less than or equal to ± (± or −) 10%, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

The term "comprising" is construed as being inclusive and open ended, and not exclusive. Specifically, the term and variations thereof mean the specified features, steps or components are included. These terms are not to be interpreted to exclude the presence of other features, steps or components.

The terms "protein" or "polypeptide" are used interchangeably and refer to molecules consisting of a chain of amino acids, without reference to a specific mode of action, size, 3 dimensional structure or origin. A "fragment" or "portion" of a protein may thus still be referred to as a "protein." An "isolated protein" is used to refer to a protein which is no longer in its natural environment, for example in vitro or in a recombinant bacterial or plant host cell.

"Plant" refers to either the whole plant or to parts of a plant, such as cells, tissue or organs (e.g. pollen, seeds, gametes, roots, leaves, flowers, flower buds, anthers, fruit, etc.) obtainable from the plant, as well as derivatives of any of these and progeny derived from such a plant by selfing or crossing.

"Plant cell(s)" include protoplasts, gametes, suspension cultures, microspores, pollen grains, etc., either in isolation or within a tissue, organ or organism. The plant cell can e.g. be part of a callus or meristem.

"Similar conditions" for culturing the plants means among other things the use of a similar temperature, humidity, nutrition and light conditions, and similar irrigation and day/night rhythm.

The terms "homology", "sequence identity" and the like are used interchangeably herein. Sequence identity is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods.

"Sequence identity" and "sequence similarity" can be determined by alignment of two peptide or two nucleotide sequences using global or local alignment algorithms, depending on the length of the two sequences. Sequences of similar lengths are preferably aligned using a global alignment algorithms (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, CA 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blossum62 for proteins and DNAFull for DNA). When sequences have a substantially different overall lengths, local alignments, such as those using the Smith Waterman algorithm, are preferred.

Alternatively percentage similarity or identity may be determined by searching against public databases, using algorithms such as FASTA, BLAST, etc. Thus, the nucleic acid and protein sequences of the present invention can further be used as a "query sequence" to perform a search against public databases to, for example, identify other family members or related sequences. Such searches can be performed using the BLASTn and BLASTx programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to oxidoreductase nucleic acid molecules of the invention. BLAST protein searches can be performed with the BLASTx program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25 (17): 3389-3402. When utilizing BLAST and Gapped BLAST programs, the default parameters of the respective programs (e.g., BLASTx and BLASTn) can be used. See the homepage of the National Center for Biotechnology Information.

The terms "nucleic acid construct" and "nucleic acid vector" are used interchangeably herein and is herein defined as a man-made nucleic acid molecule resulting from the use of recombinant DNA technology. The terms "nucleic acid construct" and "nucleic acid vector" therefore does not include naturally occurring nucleic acid molecules although a nucleic acid construct may comprise (parts of) naturally occurring nucleic acid molecules.

The term "gene" means a DNA fragment comprising a region (transcribed region), which is transcribed into an RNA molecule (e.g. an mRNA) in a cell, operably linked to suitable regulatory regions (e.g. a promoter). A gene will usually comprise several operably linked fragments, such as a promoter, a 5' leader sequence, a coding region and a 3' non-translated sequence (3' end) comprising a polyadenylation site. "Expression of a gene" refers to the process wherein a DNA region which is operably linked to appropriate regulatory regions, particularly a promoter, is transcribed into an RNA, which is biologically active, i.e. which is capable of being translated into a biologically active protein or peptide.

"Promoter" refers to a nucleic acid fragment that functions to control the transcription of one or more nucleic acids. A promoter fragment is, located upstream (5') with respect to the direction of transcription of the transcription initiation site of the gene, and is structurally identified by the presence of a binding site for DNA-dependent RNA polymerase, transcription initiation site(s) and can further comprise any other DNA sequences, including, but not limited to transcription factor binding sites, repressor and activator protein binding sites, and any other sequences of nucleotides known to one of skill in the art to act directly or indirectly to regulate the amount of transcription from the promoter.

Optionally the term "promoter" may also include the 5' UTR region (5' Untranslated Region) (e.g. the promoter may herein include one or more parts upstream of the translation initiation codon of transcribed region, as this region may have a role in regulating transcription and/or translation). A "constitutive" promoter is a promoter that is active in most tissues under most physiological and developmental conditions. An "inducible" promoter is a promoter that is physiologically (e.g. by external application of certain compounds) or developmentally regulated. A "tissue specific" promoter is only active in specific types of tissues or cells.

DETAILED DESCRIPTION OF THE INVENTION

The current invention concerns a plant cell, a plant tissue or a plant having a reduced expression of a wild-type protein, wherein the wild-type protein has at least about 75% sequence identity with SEQ ID NO: 1 over its full length. The inventors discovered that such plant cells, tissues or plants have an increased resistance to Geminiviridae as compared to an otherwise identical plant cell, plant tissue or plant expressing the wild-type protein. More in particular the inventors discovered that modifying the gene encoding this wild-type protein, resulting in a nucleic acid sequence encoding a modified protein as further detailed herein, provides for resistance against bipartite as well as monopartite members of the family Geminiviridae. In addition, the inventors discovered that the expression of a modified protein as defined herein maintains the germination potential of the plant. The invention therefore represents an important advancement in crop protection.

Hence in a first aspect, the invention concerns a plant cell, plant tissue or plant having a reduced expression of a wild type protein, wherein the protein has at least about 75% sequence identity with SEQ ID NO: 1.

A wild-type protein is defined herein as a protein that is encoded by a gene normally (i.e. naturally) present in a plant cell, plant tissue or plant, and is expressed in at least a particular developmental stage under particular environmental conditions, e.g. as it occurs in nature. The wild-type protein is thus a naturally expressed protein in its natural environment. In addition, a wild-type protein as understood herein can also be a naturally occurring protein that has first been genetically inactivated, for example by knocking-out the protein followed by reintroduction of the same protein into the plant cell, plant tissue or plant. Such normally naturally occurring protein is thus considered a wild-type protein even if it was previously reintroduced into the plant.

Preferably, the wild-type protein has at least about 75%, 80%, 85%, 90%, 95%, 96%, 97%, 98%, 99% or about 100% sequence identity with SEQ ID NO: 1. In a further embodiment the wild-type protein comprises or consists of SEQ ID NO:1. Preferably, the wild-type protein comprises or consists of a sequence selected from the group consisting of SEQ ID NO: 1 and 11-18, even more preferably, selected from the group consisting of SEQ ID NO: 1 and 11-16. In an embodiment, the wild-type protein is not SEQ ID NO: 17 and/or not SEQ ID NO:18.

Reduced expression is preferably compared to the expression level in a control plant. A control plant is defined herein as an otherwise identical plant cell, plant tissue or plant that is not modified to have a reduced expression of a protein that has at least about 75% sequence identity with SEQ ID NO: 1, e.g. the plant cell, plant tissue or plant has wild-type expression levels of the protein, preferably of the wild type protein as defined herein. In addition, the control plant also does not express the modified protein as defined herein.

Preferably, the control plant comprises the gene encoding the wild-type protein that is normally present in the plant cell, plant tissue or plant. Preferably, the control plant cell, tissue or plant is *Capsicum*, preferably a *C. annuum, C. baccatum, C. chinense, C. frutescens*, or *C. pubescens*. Preferably the control plant cell, plant tissue or plant is *C. annuum*, preferably a *C. annuum* variety Maor Plant. The plant can be a *C. annuum* variety Maor M2 plant.

In an embodiment, the expression is at least about 5%, 10%, 20%, 30%, 40%, 50%, 60%, 70%, 80%, 90%, 95% or about 100% reduced as compared to the control plant.

Reduced expression of the wild-type protein as defined herein can be accomplished by any conventional means known to the person skilled in the art. Non-limiting examples to reduce (e.g. knock-down) the expression of the wild-type protein include siRNA, epigenetic silencing, modifications of genomic regulatory sequences and/or modification or deletion of at least one nucleotide of at least one allele, preferably two alleles, of the endogenous sequence encoding the wild-type protein. Preferably, the sequence encoding the wild-type protein has at least about 75%, 80%, 85%, 90%, 95%, 96%, 97%, 98%, 99% or about 100% sequence identity with SEQ ID NO: 2.

In a preferred embodiment, the wild-type protein is not expressed, i.e. the expression is knocked-out. As a result the wild-type protein is no longer detected in the plant cell. Instead of expression of the wild-type protein, an altered, non-functional and/or truncated protein can be expressed. Knocking out the expression of the wild-type protein can be accomplished by any conventional means known to the person skilled in the art. Such conventional means include, but are not limited to, the modification or deletion of at least one nucleotide of all endogenous sequences encoding the wild-type protein. Preferably, the sequence encoding the wild-type protein has at least about 75%, 80%, 85%, 90%, 95%, 96%, 97%, 98%, 99% or about 100% sequence identity with SEQ ID NO: 2. Alternatively or in addition, the absence of the wild-type protein can be accomplished by modifying or (partially) deleting one or more regulatory sequences.

A non-limiting example of modifying or deleting the coding sequence and/or a regulatory sequence is the use of CRISPR-technology, such as CRISPR-Cas or CRISPR-Cpf1.

The expression of the wild-type protein may be reduced or knocked out by modification of a genomic regulatory sequence. As a non-limiting example, expression of the wild-type protein may be reduced or knocked out by genetic modification of a sequence having at least about has at least about 60%, 65%, 70%, 75%, 80%, 85%, 90%, 95%, 96%, 97%, 98%, 99% or about 100% sequence identity with SEQ ID NO: 8.

A genetic modification may be a mutation, such as but not limited to, at least one of an insertion, deletion or substitution of one or more base pairs, preferably at least one of an insertion, deletion or substitution of at least about 1-500, 1-400. 1-300, 1-250, 1-200, 1-150, 1-100, 1-50, 1-25, 1-20, 1-15 or at least 1-10 base pairs.

In a further embodiment a plant cell, plant tissue or plant according to the invention has a reduced expression of a wild type protein, wherein the wild type protein has at least about 75% sequence identity with SEQ ID NO: 1 over its full length, and wherein the plant cell, plant tissue or plant has an increased (viral) resistance to Geminiviridae, and wherein preferably the Geminiviridae is of the genus *Begomovirus*.

Preferably, the Geminiviridae includes at least one or more monopartite members. Preferably, the Geminiviridae includes at least one or more bipartite members. Preferably, the Geminiviridae includes at least one or more monopartite and bipartite members.

In a preferred embodiment, the invention concerns a plant cell, plant tissue or plant having a reduced expression of a wild type protein, wherein the wild type protein has at least about 75% sequence identity with SEQ ID NO: 1 over its full length, and wherein the plant cell, plant tissue or plant has an increased resistance to at least one bipartite member of the Geminiviridae family as compared to an otherwise identical plant cell, plant tissue or plant not having a reduced expression of said wild type protein. Preferably, the plant cell, plant tissue or plant has an increased resistance to at least one bipartite member and at least one monopartite member of the Geminiviridae family. Preferably, the wild type protein is not expressed in the plant cell, plant tissue or plant.

Preferably, the monopartite and/or bipartite member of Geminiviridae is a virus that is capable of infecting a plant as specified herein.

Preferably, the plant cell, plant tissue or plant according to the invention does not express the wild type protein.

Preferably, the Geminiviridae includes at least one or more members of the monopartite begomoviruses. Preferably, the Geminiviridae includes at least one or more members of the bipartite begomoviruses. Preferably, the Geminiviridae includes at least one or more members of the monopartite and bipartite begomoviruses.

In an embodiment, the monopartite and/or bipartite begomovirus is a virus that is capable of infecting a plant as specified herein.

In one embodiment, the plant cell, plant tissue or plant having a reduced expression of a wild type protein as defined herein is, or is obtainable from, a *Capsicum*, preferably a *Capsicum annuum*, wherein the plant cell, plant tissue or plant has an increased resistance to at least one member of the monopartite *Begomoviruses* capable of infecting a *Capsicum* plant. The resistance may be increased for at least 2, 3, 4, 5, 6, 7, 8, 9, or 10 members of the monopartite *Begomoviruses* capable of infecting a *Capsicum* plant.

In a further embodiment, the plant cell, plant tissue or plant according to the invention is, or is obtainable from, a *Capsicum*, preferably a *Capsicum annuum* and wherein the plant cell, plant tissue or plant has an increased resistance to at least one member of the monopartite *Begomoviruses* that is capable of infecting a *Capsicum* plant and wherein the plant cell, plant tissue or plant also has an increased resistance to at least one member of the bipartite *Begomoviruses* that is capable of infecting a *Capsicum* plant. The resistance may be increased for at least 2, 3, 4, 5, 6, 7, 8, 9, or 10 members of the monopartite *Begomoviruses* capable of infecting a *Capsicum* plant and/or for least 2, 3, 4, 5, 6, 7, 8, 9, or 10 members of the bipartite *Begomoviruses* capable of infecting a *Capsicum* plant.

In one embodiment, the plant cell, plant tissue or plant according to the invention is, or is obtainable from) a *Capsicum*, preferably a *Capsicum annuum* and the plant cell, plant tissue or plant has an increased resistance to at least one member of the bipartite *Begomoviruses* capable of infecting a *Capsicum* plant. The resistance may be increased for at least 2, 3, 4, 5, 6, 7, 8, 9, or 10 members of the bipartite *Begomoviruses* capable of infecting a *Capsicum* plant.

In one embodiment, the member of the monopartite and/or bipartite *Begomoviruses* capable of infecting a *Capsicum* plant is selected from the group consisting of Pepper Yellow Leaf Curl Virus, Pepper Leaf Curl Virus, Pepper Huasteco Yellow Vein Virus, Pepper Golden Mosaic Virus, Pepper yellow leaf curl Indonesia virus, chilli leaf curl virus, Sinaloa tomato leaf curl begomovirus, Pepper leaf curl Lahore virus, Curly top virus, Pepper mild tigre virus, pepper leaf curl Bangladesh virus, Pepper leafroll virus, Pepper yellow vein *Mali* virus, Pepper Texas begomovirus, Pepper golden mosaic begomovirus; pepper huasteco begomovirus; pepper huasteco bigeminivirus, pepper huasteco virus, Pepper huasteco yellow vein begomovirus, Pepper leaf curl Bangladesh begomovirus, pepper leaf curl begomovirus, pepper mild tigre begomovirus, pepper mild tigre bigeminivirus and pepper mild tigre geminivirus.

In a preferred embodiment, the plant cell, plant tissue or plant of the invention has increased resistance to at least one of Pepper Yellow Leaf Curl Virus, Pepper Leaf Curl Virus, Pepper Huasteco Yellow Vein Virus, Pepper Golden Mosaic Virus and/or pepper yellow leaf curl Indonesia virus.

Preferably, the plant cell, plant tissue or plant of the invention has an increased resistance to at least one of Pepper Yellow Leaf Curl Virus, Pepper Leaf Curl Virus, Pepper Huasteco Yellow Vein Virus, and Pepper Golden Mosaic Virus.

Preferably, the plant cell, plant tissue or plant of the invention has an increased resistance to at least one of Pepper Yellow Leaf Curl Virus and Pepper Leaf Curl Virus.

Preferably, the plant cell, plant tissue or plant of the invention has an increased resistance to at least one of Pepper Leaf Curl Virus, preferably strain M156 (PLCV M156), Yellow Leaf Curl Indonesian Virus (PepYLCIV), Huasteco Yellow Vein Virus (PHYVV), the Pepper Golden Mosaic Virus and the Beet curly top virus (BCTV).

In a preferred embodiment, the invention pertains to a plant cell, plant tissue or plant having a reduced expression of a wild type protein, wherein the protein has at least about 75% sequence identity with SEQ ID NO: 1 over its full length, wherein preferably the wild-type protein is not expressed and wherein the plant cell, plant tissue or plant expresses a modified protein. The modified protein preferably has a sequence that has at least about 75%, 80%, 85%, 90%, 95%, 96%, 97%, 98%, 99% or about 100% sequence identity when calculated over the positions corresponding to positions 1-66 and positions 78-308 of SEQ ID NO: 1.

In a preferred embodiment, the invention pertains to a plant cell, plant tissue or plant having a reduced expression of a wild type protein, wherein the protein has at least about 75% sequence identity with SEQ ID NO: 1 over its full length, wherein preferably the wild-type protein is not expressed and wherein the plant cell, plant tissue or plant expresses a protein that has at least about 75% sequence identity when calculated over the positions corresponding to positions 1-66 and positions 78-308 of SEQ ID NO: 1, and wherein the protein comprises a modification of one or more amino acid residues corresponding to positions 67-77 of SEQ ID NO: 1. In an embodiment, expression of the modified protein increases resistance to Geminiviridae as compared to an otherwise identical plant cell, plant tissue or plant expressing the protein without the modification.

The expression of the modified protein as defined herein may be controlled by an endogenous promoter, such as, but not limited to, the promoter controlling the expression of the wild-type protein as defined herein. Preferably, the promoter has at least about 60%, 65%, 70%, 75%, 80%, 85%, 90%, 95%, 98%, 99% or about 100% sequence identity with SEQ ID NO: 8.

Preferably, the protein comprising the modification has at least about 75%, 80%, 85%, 90%, 95%, 96%, 97%, 98% or 99% sequence identity with SEQ ID NO: 1, and preferably the modified protein has at least about 85%, 90%, 95%, 96%, 97%, 98%, or about 99% sequence identity with SEQ ID NO: 1 over its full length. Preferably, the protein has about 99.2% sequence identity with SEQ ID NO: 1. Preferably, SEQ ID NO: 1 corresponds to NCBI accession number XP_016572281.1.

In a preferred embodiment, the invention pertains to a plant cell, plant tissue or plant having a reduced expression of a wild type protein, wherein the protein has at least about 75% sequence identity with SEQ ID NO: 1 over its full length, and wherein preferably the wild-type protein is not expressed.

The plant, plant tissue or plant cell preferably expresses a modified protein that is a truncated protein. The truncated protein may comprise or consist of the N-terminal sequence, preferably the at least 10, 15, 20, 30, 40, 50, 60, 70, 80, 90 100, 150, 200, 250, 300 or 350 N-terminal amino acids, of the wild-type protein. Preferably, the plant, plant tissue or plant cell expresses a modified protein that has at least about 75% sequence identity with SEQ ID NO: 1, wherein the protein is a truncated protein having a deletion corresponding to positions 309-378 of SEQ ID NO: 1. Preferably, the plant, plant tissue or plant cell expresses a modified protein that has at least about 75% sequence identity when calculated over the positions corresponding to positions 1-66 and positions 78-308 of SEQ ID NO: 1 and wherein the protein is a truncated protein having a deletion corresponding to positions 309-378 of SEQ ID NO: 1. In an embodiment, expression of the truncated protein increases resistance to Geminiviridae as compared to an otherwise identical plant cell, plant tissue or plant expressing the protein without the truncation.

Preferably, the truncated protein has at least about 75% sequence identity when calculated over the positions corresponding to positions 1-66 and positions 78-298 of SEQ ID NO: 1 and wherein the protein is a truncated protein having a deletion corresponding to the positions of SEQ ID NO: 1 selected from the group consisting of 299-378, 300-378, 301-378, 302-378, 303-378, 304-378, 305-378, 306-378, 307-378, 308-378, 309-378, 310-378, 311-378, 312-378, 313-378, 314-378, 315-378, 316-378, 317-378, 318-378, 319-378 and 320-378. Preferably, the truncated protein has at least about 75% sequence identity when calculated over the positions corresponding to positions 1-66 and positions 78-304 of SEQ ID NO: 1 and wherein the protein is a truncated protein having a deletion corresponding to the positions of SEQ ID NO: 1 selected from the group consisting of 305-378, 306-378, 307-378, 308-378, 309-378, 310-378, 311-378, 312-378, and 313-378.

Preferably the truncation is an absence of the amino acid residues corresponding to the position of SEQ ID NO: 1 selected from the group consisting of 299, 300, 301, 302, 303, 304, 305, 306, 307, 308, 309, 310, 311, 312, 313, 314, 315, 316, 317, 318 or 319 up to and including the amino acid residues corresponding to the position of SEQ ID NO: 1 selected from the group consisting of 360, 361, 362, 363, 364, 365, 366, 367, 368, 369, 370, 371, 372, 373, 374, 375, 376, 377 and 378.

Preferably, the truncation is due to the presence of a stop codon in the DNA molecule encoding the truncated protein. Preferably, there is a stop codon in a DNA molecule having at least 75%, 80%, 85%, 90%, 95%, 96%, 97%, 98% or 99% sequence identity with position SEQ ID NO: 2 when calculated over the positions corresponding to positions 1-915 (preferably positions 1-924) and wherein a stop codon is present at a position corresponding to the position selected from the group consisting of 916-918, 919-921, 922-924, 925-927, 928-930, 931-933 and 934-936. Preferably, the stop codon is present at a position corresponding to positions 925-927 of SEQ ID NO: 2.

Preferably, the truncated protein has at least has at least 75%, 80%, 85%, 95% 96%, 97%, 98%, 99% or 100% sequence identity with SEQ ID NO: 1 when calculated over the positions corresponding to positions 1-308 of SEQ ID NO: 1.

Preferably, the modified protein only comprises a truncation as defined herein.

In a preferred embodiment the protein without the modification and/or without the truncation comprises or consists of the same amino acid sequence of the wild-type protein. Thus, the wild-type protein can be the same protein as the protein without the modification as defined herein. Hence in a preferred embodiment, the invention pertains to a plant cell, plant tissue or plant expressing a modified protein that has at least about 75% sequence identity with SEQ ID NO: 1 over its full length, and wherein the protein comprises a modification of one or more amino acid residues corresponding to positions 67-77 of SEQ ID NO: 1; or the modified protein is a truncated protein having a deletion corresponding to positions 309-378 of SEQ ID NO: 1, wherein the modification or truncation increases resistance to Geminiviridae as compared to an otherwise identical plant cell, plant tissue or plant expressing the protein without the modification or without the truncation, and wherein the protein without the modification or without the truncation is a wild type version of the protein. Preferably, the plant cell, plant tissue or plant expressing the modified protein does not express the wild type version of the protein.

The plant cell, tissue or plant as defined herein can comprise a modified protein, wherein the modified protein i) has at least about 75% sequence identity with SEQ ID NO: 1 over its full length, and wherein the modified protein comprises a modification of one or more amino acid residues corresponding to positions 67-77 of SEQ ID NO: 1 or ii) wherein the modified protein is a truncated protein having at least 75% sequence identity when calculated over the positions corresponding to positions 1-308 of SEQ ID NO: 1 and wherein the truncated protein has a deletion corresponding to positions 309-378 of SEQ ID NO: 1.

Alternatively, the plant cell, tissue or plant as defined herein can comprise at least two different modified proteins, wherein i) one modified protein has at least about 75% sequence identity with SEQ ID NO: 1 over its full length and wherein the modified protein comprises a modification of one or more amino acid residues corresponding to positions 67-77 of SEQ ID NO: 1 and ii) a second modified protein which is a truncated protein having at least 75% sequence identity when calculated over the positions corresponding to positions 1-308 of SEQ ID NO: 1 and wherein the truncated protein has a deletion corresponding to positions 309-378 of SEQ ID NO: 1.

A modified protein is herein understood as at least one of:

i) A protein having at least about 75% sequence identity when calculated over the positions corresponding to positions 1-66 and positions 78-308 of SEQ ID NO: 1 and wherein the modified protein comprises a modification of one or more amino acid residues corresponding to positions 67-77 of SEQ ID NO: 1; and ii) A truncated protein having at least about 75% sequence identity when calculated over the positions corresponding to positions 1-66 and positions 78-308 of SEQ ID NO: 1 and wherein the truncated protein has a deletion corresponding to positions 309-378 of SEQ ID NO: 1, unless it is clearly indicated in the text that only the protein comprising the modification or only the protein comprising the truncation is intended.

In an embodiment, the plant cell, tissue or plant comprising the modified protein has an increased resistance to Geminiviridae as compared to the same plant cell, plant tissue or plant that does not express the modified protein, e.g. an otherwise identical plant. Preferably the plant cell, tissue or plant expressing the modified protein is grown under the same conditions as the otherwise identical plant cell, plant tissue or plant.

In an embodiment, the protein comprises a modification of one or more amino acid residues at positions 68-76, 69-75, 70-74, preferably at positions 71-73 of SEQ ID NO: 1. Preferably, the modified protein comprises only a modification of one or more amino acid residues at positions 68-76, 69-75, 70-74, preferably at positions 71-73 of SEQ ID NO: 1. One or more amino acid modifications is herein understood as that the modified protein can comprises one, two, three, four, five, six, seven, eight, nine or ten amino acid modifications in the residues corresponding to positions 67-77 of SEQ ID NO: 1. Hence, there is a modification at least at one of position 67, 68, 69, 70, 71, 72, 73, 74, 75, 76 and 77 of SEQ ID NO: 1.

A modification can be a substitution of one or more amino acid residues in said region with a different naturally or non-naturally occurring amino acid residue. Hence, one amino acid residue may be substituted with one other naturally or non-naturally occurring amino acid residue. Alternatively or in addition, at least one amino acid residue at least at one of position corresponding to position 67, 68, 69, 70, 71, 72, 73, 74, 75, 76 and/or 77 of SEQ ID NO: 1 can be substituted for at least two, three, four, five, six, seven, eight, nine or ten naturally or non-naturally occurring amino acid residues. In addition, a modifications can be a deletion of an amino acid residue in said region. For example, a modification of amino acid at position 71 of SEQ ID NO: 1 can be a deletion of the amino acid residue at position 71. It can easily be determined whether a plant cell, plant tissue or plant has increased resistance to Geminiviridae using any conventional method known to the person skilled in the art.

As a non-limiting example, the increase in resistance to one or more members of the family Geminiviridae can be determined by comparing a control plant with a plant having a reduced expression of a wild type protein, wherein the wild-type protein has at least about 75% sequence identity with SEQ ID NO: 1 over its full length, under controlled conditions chosen such that in the control plant at least one sign of disease can be observed after a certain period. Such controlled conditions include e.g. infection of infestation of plants with one or more Geminiviridae viruses capable of infection and/or infestation, such as one or more members of the family Geminiviridae as defined herein.

As a further non-limiting example, the increase in resistance to one or more members the family Geminiviridae can be determined by comparing a control plant with a plant provided with the modified protein as defined herein under controlled conditions chosen such that in the control plant at least one sign of disease can be observed after a certain period. Such controlled conditions include e.g. infection or infestation of plants with one or more Geminiviridae viruses capable of infection and/or infestation, such as one or more members of the family Geminiviridae as defined herein.

In an embodiment, the plant having a reduced expression of a wild type protein as defined herein, has an increased resistance against at least 1, 2, 3, 4, 5, 6, 7, 8, 9, 10, 20, 30, 50 or all members of the family Geminiviridae. Preferably, said plant has an increased resistance to one or more bipartite members of the family Geminiviridae.

In a further embodiment, the plant expressing the modified protein has an increased resistance against at least 1, 2, 3, 4, 5, 6, 7, 8, 9, 10, 20, 30, 50 or all members of the family Geminiviridae. Preferably, said plant has an increased resistance to one or more bipartite members of the family Geminiviridae.

Under the controlled conditions chosen, the control plant shows preferably at least one sign (i.e. one symptom) of disease. Symptoms of disease are well-known to the person skilled in the art. Such symptoms include, but are not limited to stunting, distorted growth, leaf crumpling, curling, distortion, golden-light green-yellow mosaic/mottle, interveinal yellowing, discoloration (e.g. yellow spots), vein swelling, purpling, and/or yellowing after a certain period. Symptoms of the disease may include at least curling of the leaves and/or discoloration. The control plant can show at least 1, 2, 3, 4, 5, 6, 7, or 8 signs of disease after a certain period of time. Alternatively, the control plant may shows not more than 1, 2, 3, 4, 5, 6, 7, or 8 signs of disease after a certain period of time.

A certain period as used herein is preferably any period prior to the observing at least one, two or three signs of disease in the control plant and this period may be dependent on the experimental set up. Such period can be easily determined by the person skilled in the art. Preferably, such period before observing at least one, two or three signs of disease is at least about 20, 30, 35, 40, 45, 50, 60 or about 70 days. Preferably, the period before observing symptoms is about 2 weeks, 3 weeks, 1 month, 2 months 3 months, 4 months, 5 months or 6 months.

Preferably, the plant having a reduced expression of a wild type protein as defined herein will show less and/or reduced signs of disease as compared to the control plant after the certain period as defined herein.

Preferably, the plant comprising the modified protein as defined herein will show less and/or reduced signs of disease as compared to the control plant after the certain period as defined herein.

As a non-limiting example, the plant having a reduced expression of a wild type protein as defined herein, and optionally further comprising the modified protein as defined herein, may show at least one of a reduced stunting, distorted growth, leaf crumpling, curling, distortion, golden-light green-yellow mosaic/mottle, interveinal yellowing, discoloration (e.g. yellow spots), vein swelling, purpling, and yellowing, as compared to the control plants. Symptoms of the disease may include at least curling of the leaves and/or discoloration. Alternatively or in addition, the plant having a reduced expression of a wild type protein as defined herein, and optionally further comprising the modified protein as defined herein, may show one or more signs of disease as defined herein at a similar or same severity as the control plant, however the one or more signs of disease will be at a later time period as compared to the control plant, e.g. there will be a delay in one or more symptoms of the disease. As a non-limiting example, there can be a delay of at least 1, 2, 3, 4, 5, 6, 7 or 8 weeks as compared to the control plants. The skilled person knows how to select suitable conditions such as for example the controlled conditions used in the example section detailed herein below.

When a plant has an increased resistance to Geminiviridae, it is preferably capable of sustaining a normal growth and/or a normal development when the plant is subjected to infection with at least one member of the family Geminiviridae, which infection would otherwise have resulted in reduced growth and/or reduced development of the plant. Hence, an increased resistance to Geminiviridae can be determined by comparing plants. As a non-limiting example, one plant having a reduced expression of a wild type protein as defined herein, and optionally further expressing a modified protein as defined herein can be compared with one control plant. Alternatively or in addition, a group of plants having a reduced expression of a wild type protein as defined herein, and optionally further expressing a modified protein as defined herein may be compared with a group of control plants. Each group can comprise e.g. at least 2, 3, 4, 5, 10, 15, 20, 25, 50 or 100 individual plants.

The skilled person is well aware how to select appropriate conditions to determine increased resistance to Geminiviridae and how to measure signs of infection. As a non-limiting example, resistance to a member of the family Geminivirdae can be measured by visual inspection, e.g. for discoloration and/or leaf curling.

In an embodiment, resistance against at least one member of the family Geminiviridae is determined by counting the number of discolored leaves after infection with at least one member of the family Geminivirdae, preferably under the conditions as defined herein. In comparison to a control plant as defined herein, the number of discolored leafs is less or (virus induced) discolored leafs are absent in a plant having a reduced expression of a wild type protein as defined herein, and optionally further expressing the modified protein as defined herein.

The skilled person knows how to assess the discoloration of the leafs after virus infection. As a non-limiting example, the amount of discoloration can be determined by visual inspection or by counting the leafs showing discoloration. As a non-limiting example, a leaf is counted as discolored if the leaf has at least one (virus-induced) discolored spot. Alternatively, a leaf is showing discoloration if the leaf has at least 2, 3, 4, 5, 6 or 7 virus-induced discolored spots. The diameter of the discolored spot can preferably be at least 10 mm, 25 mm, 50 mm, 1 cm or at least 5 cm. In another embodiment, the surface of the discoloration spot is at least 10 mm, 25 mm, 50 mm, 1 cm or at least 5 cm.

An infected control plant can have a virus-induced discoloration of at least one leaf. Alternatively, an infected control plant has at least 1, 2, 3, 4, 5, 6, 7, 8, 9 or 10 discolored leaves. The plant having a reduced expression of a wild type protein as defined herein, and optionally further expressing the modified protein as defined herein preferably does not show any (virus induced) discolored leaves. Alternatively, the plant having a reduced expression of said wild type protein and optionally further expressing the modified protein can have fewer discolored leafs as compared to number of leaves of the infected control plant. Preferably, the number of (virus-induced) discolored leaves is less than 80%, 60%, 50%, 40%, 30%, 20%, 10%, 5%, 2% or 1% of the number of discolored leafs of the infected control plant.

Alternatively or in addition, the leafs of the control plant have more discolored spots per leaf as compared to the leafs of a plant having a reduced expression of a wild type protein as defined herein, and optionally further expressing the modified protein as defined herein. The degree of discoloration of all leafs of a control plant can be compared with the discoloration of all leafs of the plant having a reduced expression of a wild type protein as defined herein, and optionally further expressing the modified protein as defined herein. The degree of discoloration of all plant leafs can be determined by visual inspection or by counting the number of discolored spots as defined herein above and dividing the number of spots by the number of leafs per plant.

Alternatively or additionally, resistance to a member of the family Geminivirdae can be measured by visual inspection for leaf curling. In an embodiment, resistance against at least one member of the family Geminiviridae is determined by counting the number of curled leaves after infection with at least one member of the family Geminivirdae, preferably under the conditions as defined herein. In comparison to a control plant as defined herein, the number of curled leafs is less or (virus induced) curled leafs are absent in a plant having a reduced expression of a wild type protein as defined herein, and optionally further expressing the modified protein as defined herein.

The skilled person knows how to assess the curling of the leafs after virus infection. As a non-limiting example, the degree of curling can be determined by counting the number of curled leafs. An infected control plant can have a virus-induced curling of at least one leaf. Alternatively, an infected control plant has at least 1, 2, 3, 4, 5, 6, 7, 8, 9 or 10 curled leaves. The plant having a reduced expression of a wild type protein as defined herein, and optionally further expressing the modified protein as defined herein, preferably does not show any (virus induced) curled leaves. Alternatively, the plant having a reduced expression of a wild type protein as defined herein, and optionally further expressing the modified protein can have fewer curled leafs as compared to number of leaves of the infected control plant. Preferably, the number of (virus-induced) curled leaves is less than 80%, 60%, 50%, 40%, 30%, 20%, 10%, 5%, 2% or 1% of the number of discolored leafs of the infected control plant.

The percentage of resistant plants can be determined by counting the number of disease free plants. In an embodiment, the number of disease-free plants having a reduced expression of a wild type protein as defined herein, and optionally further expressing the modified protein, is determined. Preferably, plants having a reduced expression of a wild type protein as defined herein, and optionally further expressing the modified protein, are exposed to at least one member of the family Geminiviridae and the number of disease-free plants is at least about 5%, 10%, 15%, 20%, 25%, 30%, 35%, 40%, 45%, 50%, 55%, 60%, 65%, 70%, 75%, 80%, 85%, 90%, 95%, 98%, 99% or about 100% of the number of plants prior to exposure with a member of the family Geminiviridae. In a further embodiment, resistance against at least one member of the family Geminiviridae can be determined by a PCR-based detection of the member or members of the Geminiviridae, such as described by example 2.

In an embodiment, the relative titer of at least one member of the family Geminiviridae can be determined in an infested susceptible plant. In addition, the relative titer of the same at least one member of the family Geminiviridae can be determined in an infested plant having a reduced expression of a wild type protein as defined herein, and wherein the plant optionally further expresses the modified protein as defined herein. The titer obtained from the susceptible plant can be compared with the titer obtained from the plant having a reduced expression of a wild type protein as defined herein, and wherein the plant optionally further expresses the modified protein. In a preferred embodiment, the titer obtained from the susceptible plant is set to 100% and preferably the titer obtained from the resistant plant is at most (not more than) about 50%, 40%, 30%, 20%, 10%, 5%, 4%, 3%, 2.5%, 2%, 1.5%, 1%, 0.5% or about 0.1% compared to the titer obtained from the susceptible plant.

The relative titer can be determined using any conventional method known in the art, including but not limited to qPCR-based detection.

In an embodiment, resistance against at least one member of the family Geminiviridae can be determined as described by Scott et al (Introgression of resistance to whitefly-transmitted geminiviruses from *Lycopersicon chilense* to tomato (1996), p. 357-367. In: Gerling, D. and R. T. Mayer (eds.). *Bemisia* 1995: Taxonomy, biology, damage control, and management. Intercept Ltd., Andover, Hants, UK) and/or Lapidot et al ("Development of a Scale for Evaluation of Tomato yellow leaf curl virus Resistance Level in Tomato Plants", Phytopathology (2006) 96(12): 1404-8. Resistance can be measured by rating the disease severity on a 0 to 4 disease severity index scale. For example, is the disease severity is scored 0, the plant is considered to be resistant. The scale is divided as presented in table 1.

TABLE 1

| Disease severity correlated to resistance to *Geminiviridae*. | | |
| --- | --- | --- |
| Score | Visibility of symptoms | Resistance |
| 0 | No symptoms | Resistant |
| 1 | slight symptoms visible only upon close inspection | resistant |
| 2 | moderate symptoms, on part of the plant only, visible from 2-3 meters | Intermediate |
| 3 | symptoms on entire plant, some stunting of the plant | Symptoms/ Susceptible |
| 4 | severe symptoms on the entire plant and severe stunting | Symptoms/ Susceptible |

In a preferred embodiment, at least about 10%, 20%, 30%, 40%, 50%, 60%, 70%, 80%, 90% or 100% of the plants having a reduced expression of a wild type protein as defined herein, and optionally further expressing the modified protein as defined herein, score 0-2, preferably 0-1, when grown under the same conditions wherein at least about 60%, 70%, 80%, 90% or 100% of the control plants score 3-4.

In a preferred embodiment, at least about 10%, 20%, 30%, 40%, 50%, 60%, 70%, 80%, 90% or 100% of the plants having a reduced expression of a wild type protein as defined herein, and optionally further expressing the modified protein as defined herein, score 3, when grown under the same conditions wherein at least about 60%, 70%, 80%, 90% or 100% of the control plants score 4.

In a preferred embodiment, at least about 10%, 20%, 30%, 40%, 50%, 60%, 70%, 80%, 90% or 100% of the plants having a reduced expression of a wild type protein as defined herein, and optionally further expressing the modified protein as defined herein, score 2, when grown under the same conditions wherein at least about 60%, 70%, 80%, 90% or 100% of the control plants score 4.

In a preferred embodiment, at least about 10%, 20%, 30%, 40%, 50%, 60%, 70%, 80%, 90% or 100% of the plants having a reduced expression of a wild type protein as defined herein, and optionally further expressing the modified protein as defined herein, score 1, when grown under the same conditions wherein at least about 60%, 70%, 80%, 90% or 100% of the control plants score 4.

In a preferred embodiment, at least about 10%, 20%, 30%, 40%, 50%, 60%, 70%, 80%, 90% or 100% of the plants having a reduced expression of a wild type protein as defined herein, and optionally further expressing the modified protein as defined herein, score 0, when grown under the same conditions wherein at least about 60%, 70%, 80%, 90% or 100% of the control plants score 4.

In an embodiment, at most about 0%, 1%, 5%, 10%, 15%, 20%, 30%, 40%, 50% or at most about 60% of the plants having a reduced expression of a wild type protein as defined herein, and optionally further expressing the modified protein as defined herein, score 3 or 4 when grown under the same conditions wherein at least about 90%, 95% or 100% of the control plants score 3 or 4.

In another embodiment, at most about 0%, 1%, 5%, 10%, 15%, 20%, 30%, 40%, 50% or at most about 60% of the plants having a reduced expression of a wild type protein as defined herein, and optionally further expressing the modified protein as defined herein, score 3 or 4 when grown under the same conditions wherein at least about 90%, 95% or 100% of the control plants score 3 or 4 and wherein at least 1%, 5%, 10%, 15%, 20%, 30%, 40% of the plants having a reduced expression of a wild type protein as defined herein, and optionally further expressing the modified protein, score 0 or 1.

In yet another embodiment, resistance against at least one member of the family Geminiviridae is determined as described in e.g. Obaiah et al. (2013) *Screening of some blackgram(Vignamungo(L.)Hepper) genotypes for resistance to yellow mosaic virus*. Current Biotica 7 (1&2): p 96-100), which is hereby incorporated by reference, by rating the disease severity on a scale from 1-9, whereby plants classified a "9" are fully susceptibly and those classified with a "1" are symptomless. In a preferred embodiment, at least about 10%, 20%, 30%, 40%, 50%, 60%, 70%, 80%, 90% or 100% of the plants having a reduced expression of a wild type protein as defined herein, and optionally further expressing the modified protein as defined herein, score 1-3, preferably 1-2, when grown under the same conditions wherein at least about 60%, 70%, 80%, 90% or 100% of the control plants score 6-9, preferably 7-9 or 8-9.

In a further embodiment, a plant cell, plant tissue or plant according to the invention, is a plant cell, plant tissue or plant having a reduced expression of a wild type protein as defined herein, and optionally further comprising a modified protein as defined herein, and wherein the germination potential remains similar to the germination potential of an otherwise identical plant cell, plant tissue or plant expressing the protein without the modification. Preferably, the modified protein is a modification of one or more amino acid residues corresponding to positions 67-77 of SEQ ID NO: 1 as defined herein.

The terms "germination potential" or "germination rate" can be used interchangeably herein and is herein defined as the number of seeds of a particular plant species, variety or seedlot that are likely to germinate over a given period. It is a measure of germination time course and is usually expressed as a percentage, e.g., an 85% germination rate indicates that about 85 out of 100 seeds will probably germinate under proper conditions over the germination period given. When used in the context of the invention, the germination potential of a plant having a reduced expression of a wild type protein as defined herein, and optionally further expressing the modified protein as defined herein, remains preferably similar to the germination potential of a control plant a, e.g. a plant that is an otherwise identical plant cell, plant tissue or plant expressing the protein without the modification. A similar germination potential is preferably herein understood as a germination percentage that differs no more than about 0.1%, 0.5%, 1%, 2%, 3%, 4%, 5%, 10%, 15% or 20% as compared to the germination percentage of the control plant. Preferably, the seeds of a control plant and the seeds of a plant having a reduced expression of a wild type protein as defined herein, and optionally further expressing the modified protein as defined herein, are stored under the same conditions. Preferably, the seeds of a control plant and the seeds of a plant having a reduced expression of a wild type protein as defined herein, and optionally further expressing the modified protein as defined herein, are germinated under the same conditions and/or the same germination period given.

In a further embodiment, the invention concerns a plant cell, plant tissue or plant having a reduced expression of a wild type protein as defined herein, and optionally further comprising a modified protein as defined herein, wherein at least one modification is a deletion of one or more amino acid residues at a position corresponding to positions 67-77 of SEQ ID NO: 1. In a further embodiment, the modified protein comprises a deletion of one or more amino acid residues corresponding to positions 68-76, 69-75, 70-74, preferably to positions 71-73 of SEQ ID NO: 1. One or more amino acid deletions is herein understood as that the modified protein can comprise one, two, three, four, five, six, seven, eight, nine or ten amino acid deletions of the residues corresponding to positions 67-77 of to SEQ ID NO: 1.

In a preferred embodiment, the modification is a deletion of at least one, two or three amino acid residues at the positions indicated herein. Preferably, the modification is the deletion of at least one amino acid residue corresponding to position 71, 72 or 73 of SEQ ID NO: 1. More preferably, the modification is the deletion of at least two amino acid residues corresponding to position 71, 72 or 73 of SEQ ID NO: 1, i.e. the deletion of the residues corresponding to positions 71 and 72; 72 and 73; or 71 and 73. Even more preferred, the modification is the deletion of the three amino acid residues corresponding to positions 71, 72 and 73 of SEQ ID NO: 1.

In a further embodiment, the modified protein has at least about 75%, 80%, 85%, 90%, 95%, 96%, 97%, 98%, 99% or 100% sequence identity when calculated over the positions corresponding to positions 1-66 of SEQ ID NO: 1. In addition or alternatively, the modified protein as defined herein has at least about 75%, 80%, 85%, 90%, 95%, 96%, 97%, 98%, 99% or 100% sequence identity when calculated over the positions corresponding positions 78-378 of SEQ ID NO: 1.

In yet another embodiment the modified protein as defined herein is encoded by a nucleic acid comprising a sequence having at least about 75%, 80%, 85%, 90%, 95%, 96%, 97%, 98%, 99% or 100% sequence identity with SEQ ID NO: 4. Hence, the modified protein as defined herein is preferably expressed from a nucleic acid comprising a sequence having at least about 75%, 80%, 85%, 90%, 95%, 96%, 97%, 98%, 99% or 100% sequence identity with SEQ ID NO: 4.

In an embodiment, the protein without the modification is encoded by a nucleotide sequence having at least about 75%, 80%, 85%, 90%, 95%, 96%, 97% or, 98%, 99% or 100% sequence identity with SEQ ID NO: 2. As the protein without a modification can be a wild-type protein, the nucleotide sequence of the protein without a modification can correspond to an endogenous mRNA sequence that has been converted into cDNA.

In an embodiment, the nucleic acid encoding the modified protein as defined herein comprises a sequence having at least about 75%, 80%, 81.5%, 85%, 90%, 95%, 96%, 97%, 98%, 99 or 99.2% sequence identity with SEQ ID NO: 2. In addition or alternatively, the nucleic acid encoding the protein without the modification comprises a sequence having at least about 75%, 80%, 85%, 90%, 95%, 96%, 97% or 98% sequence identity with SEQ ID NO: 4. In a further embodiment, wherein the modified protein is a truncated protein and wherein the truncated protein has at least about 75%, 80%, 85%, 90%, 95%, 96%, 97%, 98%, 99% or 100% sequence identity when calculated over the positions corresponding to positions 1-308 of SEQ ID NO: 1.

In yet another embodiment the modified protein as defined herein is a truncated protein and encoded by a nucleic acid comprising a sequence having at least about 75%, 80%, 85%, 90%, 95%, 96%, 97%, 98%, 99% or 100% sequence identity with SEQ ID NO: 5. Hence, the truncated protein as defined herein is preferably expressed from a nucleic acid comprising a sequence having at least about 75%, 80%, 85%, 90%, 95%, 96%, 97%, 98%, 99% or 100% sequence identity with SEQ ID NO: 6.

In a further embodiment a plant cell, plant tissue or plant according to the invention has a reduced expression of a wild type protein as defined herein, and optionally further comprises a modified protein as defined herein, wherein the modified protein increases the (viral) resistance to Geminiviridae, and wherein preferably the Geminiviridae is of the genus *Begomovirus*.

In one embodiment, the modified protein increases the resistance to at least one or more members of the monopartite begomoviruses. In a further embodiment, the modified protein increases the resistance to at least one or more members of the monopartite and bipartite begomoviruses. Preferably, the modified protein as defined herein increases resistance to at least one or more bipartite members of begomavirus. In an embodiment, the monopartite and/or bipartite begomovirus is a virus that is capable of infecting a plant as specified herein. Preferably, the plant cell, plant tissue or plant according to the invention encodes homozygously for the modified protein of the invention.

In one embodiment, the modified protein increases the resistance to at least one or more members of a monopartite Geminiviridae.

Preferably, the modified protein as defined herein increases resistance to at least one or more bipartite members of Geminiviridae. In a further embodiment, the modified protein increases the resistance to at least one or more members of a monopartite and a bipartite Geminiviridae. In an embodiment, the monopartite and/or the bipartite member of Geminiviridae is a virus that is capable of infecting a plant as specified herein.

Preferably, the plant cell, plant tissue or plant expressing the modified protein as defined herein, is a dicotyledonous crop. The terms "dicotyledonous" and "dicot" may be used interchangeably herein. Preferably, the dicotyledonous crop is selected from the group consisting of *Capsicum, Solanum lycopersicum, Glycine max Manihot esculenta, Gossypium,* Cucurbitaceae, *Solanum melongena, Abelmoschus esculentus,* Fabaceae and *Arabidopsis.*

The invention is not limited to any specific plant cell, plant tissue or plant. It is understood herein that the invention equally applies to other plant cells, plant tissues or plants, i.e. any reference to "*Capsicum*" as detailed herein, equally applies to any other dicotyledonous crop, preferably also applies to at least one of *Glycine max, Solanum lycopersicum, Manihot esculenta, Gossypium,* Cucurbitaceae, *Solanum melongena, Abelmoschus esculentus,* Fabaceae and *Arabidopsis.* Preferably, any reference to "*Capsicum*" as detailed herein, equally applies to at least one of *Glycine max, Manihot esculenta, Gossypium* and Cucurbitaceae. Preferably, any reference to "*Capsicum*" as detailed herein, equally applies to at least *Manihot esculenta* and *Gossypium.* In some embodiments, a reference to "*Capsicum*" as detailed herein, does not apply to *Solanum lycopersicum* and *Arabidopsis.*

It is to be understood herein, that when the invention as defined herein applies to *Solanum lycopersicum,* the wild-type protein preferably has at least about 75%, 80%, 85%, 90%, 95%, 96%, 97%, 98%, 99% or about 100% sequence identity with SEQ ID NO: 18, when the invention applies to *Manihot esculenta,* the wild-type protein preferably has at least about 75%, 80%, 85%, 90%, 95%, 96%, 97%, 98%, 99% or about 100% sequence identity with SEQ ID NO: 12, when the invention applies to *Gossypium,* the wild type protein preferably has at least about 75%, 80%, 85%, 90%, 95%, 96%, 97%, 98%, 99% or about 100% sequence identity with at least one of SEQ ID NO: 13 and 14, when the invention applies to *Arabidopsis thaliana* the wild type protein preferably has at least about 75%, 80%, 85%, 90%, 95%, 96%, 97%, 98%, 99% or about 100% sequence identity with SEQ ID NO: 17, when the invention applies to Cucurbitaceae, the wild type protein preferably has at least about 75%, 80%, 85%, 90%, 95%, 96%, 97%, 98%, 99% or about 100% sequence identity with SEQ ID NO: 11, and when the invention applies to *Glycine max,* the wild type protein preferably has at least about 75%, 80%, 85%, 90%, 95%, 96%, 97%, 98%, 99% or about 100% sequence identity with at least one of SEQ ID NO: 15 and 16.

It is further to be understood herein, that when the invention as defined herein applies to *Solanum lycopersicum,* the wild-type protein preferably is encoded by a sequence having has at least about 75%, 80%, 85%, 90%, 95%, 96%, 97%, 98%, 99% or about 100% sequence identity with SEQ ID NO: 26, when the invention applies to

*Manihot esculenta,* the wild-type protein preferably is encoded by a sequence having at least about 75%, 80%, 85%, 90%, 95%, 96%, 97%, 98%, 99% or about 100% sequence identity with SEQ ID NO: 20, when the invention applies to *Gossypium,* the wild type protein preferably is encoded by a sequence having at least about 75%, 80%, 85%, 90%, 95%, 96%, 97%, 98%, 99% or about 100% sequence identity with at least one of SEQ ID NO: 21 and 22, when the invention applies to *Arabidopsis thaliana* the wild type protein preferably is encoded by a sequence having at least about 75%, 80%, 85%, 90%, 95%, 96%, 97%, 98%, 99% or about 100% sequence identity with SEQ ID NO: 25, when the invention applies to Cucurbitaceae, the wild type protein preferably is encoded by a sequence having at least about 75%, 80%, 85%, 90%, 95%, 96%, 97%, 98%, 99% or about 100% sequence identity with SEQ ID NO: 19, and when the invention applies to *Glycine max,* the wild type protein preferably is encoded by a sequence having at least about 75%, 80%, 85%, 90%, 95%, 96%, 97%, 98%, 99% or about 100% sequence identity with at least one of SEQ ID NO: 23 and 24.

In one embodiment the plant cell, plant tissue or plant is or is obtainable from a *Capsicum* plant, preferably the plant cell, plant tissue or plant is a *Capsicum* plant cell, plant tissue or plant. Preferably the plant cell, plant tissue or plant is, or is obtainable from, a *C. annuum, C. baccatum, C. chinense, C. frutescens,* or *C. pubescens.* More preferably the plant cell, plant tissue or plant is, or is obtainable from, a *C. annuum.*

Similarly in one embodiment, the plant cell, plant tissue or plant is, or is obtainable from, a *Gossypium* plant, preferably the plant cell, plant tissue or plant is a *Gossypium* plant cell, plant tissue or plant. Preferably the plant cell, plant tissue is, or is obtainable from, a *G. hirsutum, G. barbadense, G. arboretum* or *G. herbaceum.* Preferably, the plant cell, plant tissue or plant is, or is obtainable from, a *G. hirsutum.*

In one embodiment the plant cell, plant tissue or plant is or is obtainable from a Cucurbitaceae plant, preferably the plant cell, plant tissue or plant is a Cucurbitaceae plant cell, plant tissue or plant. Preferably the plant cell, plant tissue or plant is, or is obtainable from, a *Cucurbita pepo, Cucurbita moschata, Cucumis melo* or *Cucumis sativus.* More preferably the plant cell, plant tissue or plant is, or is obtainable from, *Cucurbita pepo.*

In one embodiment, the plant cell, plant tissue or plant according to the invention is (or is obtainable from) a *Capsicum,* preferably a *Capsicum annuum.* Preferably, the plant has a reduced expression of a wild type protein as defined herein, and optionally further expresses a modified protein as defined herein, and the modified protein increases the resistance to at least one member of the monopartite *Begomoviruses* capable of infecting a *Capsicum* plant. The modified protein may increase the resistance to at least 2, 3, 4, 5, 6, 7, 8, 9, or 10 members of the monopartite *Begomoviruses* capable of infecting a *Capsicum* plant.

In a further embodiment, the plant cell, plant tissue or plant according to the invention is (or is obtainable from) a *Capsicum,* preferably a *Capsicum annuum* and wherein the plant has a reduced expression of a wild type protein as defined herein, and optionally further expresses a modified protein as defined herein, and the modified protein increases the resistance to at least one member of the monopartite *Begomoviruses* that is capable of infecting a *Capsicum* plant and wherein the modified protein also increases the resistance to at least one member of the bipartite *Begomoviruses* that is capable of infecting a *Capsicum* plant. The modified protein may increase the resistance to at least 2, 3, 4, 5, 6, 7, 8, 9, or 10 members of the monopartite *Begomoviruses* capable of infecting a *Capsicum* plant and/or at least 2, 3, 4, 5, 6, 7, 8, 9, or 10 members of the bipartite *Begomoviruses* capable of infecting a *Capsicum* plant.

In one embodiment, the plant cell, plant tissue or plant according to the invention is, or is obtainable from, a *Capsicum*, preferably a *Capsicum annuum* and the modified protein increases the resistance to at least one member of the bipartite *Begomoviruses* capable of infecting a *Capsicum* plant. The modified protein may increase the resistance to at least 2, 3, 4, 5, 6, 7, 8, 9, or 10 members of the bipartite *Begomoviruses* capable of infecting a *Capsicum* plant.

In one embodiment, the member of the monopartite and/or bipartite *Begomoviruses* capable of infecting a *Capsicum* plant is selected from the group consisting of Pepper Yellow Leaf Curl Virus, Pepper Leaf Curl Virus, Pepper Huasteco Yellow Vein Virus, Pepper Golden Mosaic Virus, Pepper yellow leaf curl Indonesia virus, chilli leaf curl virus, Sinaloa tomato leaf curl begomovirus, Pepper leaf curl Lahore virus, Curly top virus, Pepper mild tigre virus, pepper leaf curl Bangladesh virus, Pepper leafroll virus, Pepper yellow vein *Mali* virus, Pepper Texas begomovirus, Pepper golden mosaic begomovirus; pepper huasteco begomovirus; pepper huasteco bigeminivirus, pepper huasteco virus, Pepper huasteco yellow vein begomovirus, Pepper leaf curl Bangladesh begomovirus, pepper leaf curl begomovirus, pepper mild tigre begomovirus, pepper mild tigre bigeminivirus and pepper mild tigre geminivirus.

In a preferred embodiment, the plant cell, plant tissue or plant of the invention has increased resistance to at least one of Pepper Yellow Leaf Curl Virus, Pepper Leaf Curl Virus, Pepper Huasteco Yellow Vein Virus, Pepper Golden Mosaic Virus and/or pepper yellow leaf curl Indonesia virus.

Preferably, the modified protein increases the resistance to at least one of Pepper Yellow Leaf Curl Virus, Pepper Leaf Curl Virus, Pepper Huasteco Yellow Vein Virus, and Pepper Golden Mosaic Virus.

In a preferred embodiment, the modified protein as defined herein increases the resistance to at least one of Pepper Yellow Leaf Curl Virus, Pepper Leaf Curl Virus, Pepper Huasteco Yellow Vein Virus, Pepper Golden Mosaic Virus and/or pepper yellow leaf curl Indonesia virus. In a more preferred embodiment the modified protein increases the resistance to at least one of Pepper Yellow Leaf Curl Virus, Pepper Leaf Curl Virus, Pepper Huasteco Yellow Vein Virus, and Pepper Golden Mosaic Virus. In an even more preferred embodiment the modified protein increases the resistance to Pepper Yellow Leaf Curl Virus and/or Pepper Leaf Curl Virus.

Preferably, the modified protein as defined herein increases the resistance to at least one of Pepper Leaf Curl Virus, preferably strain M156 (PLCV M156), Yellow Leaf Curl Indonesian Virus (PepYLCIV), Huasteco Yellow Vein Virus (PHYVV), the Pepper Golden Mosaic Virus and the Beet curly top virus (BCTV).

In a second aspect, invention pertains to a modified protein as defined herein.

In one embodiment, the modified protein has at least about 75%, 80%, 85%, 90%, 95% 98% or 99% sequence identity with SEQ ID NO: 1 over its full length and comprises a modification of one or more amino acid residues corresponding to positions 67-77 of SEQ ID NO: 1 as defined herein.

Preferably, the modified protein has at least about 75%, 80%, 85%, 90%, 95% 98%, 99% or 100% sequence identity when calculated over the positions corresponding to positions 1-66 and positions 78-308 of SEQ ID NO: 1 and wherein the modified protein comprises a modification of one or more amino acid residues corresponding to positions 67-77 of SEQ ID NO: 1. Preferably the modified protein, when expressed in a plant cell, plant tissue or plant as defined herein increases resistance to Geminiviridae as compared to an otherwise identical plant cell, plant tissue or plant expressing the protein without the modification.

Preferably, the modified protein does not comprise or consist of UniProt sequence A0A068TUH6. In addition or alternatively, the modified protein does not comprise or consist of SEQ ID NO: 9 or 10 as disclosed in WO2014/ 045206.

Preferably, the modified protein comprises an amino acid sequence having at least about 75%, 80%, 85%, 90%, 95%, 98%, 99% or about 100% sequence identity with SEQ ID NO: 3. Preferably, the protein comprises or consists of the amino acid sequence of SEQ ID NO: 3. The modified protein as defined herein can be an isolated protein or the protein can be present in a cell, e.g. in a plant cell as defined herein. Preferably, the modified protein is present in a *Capsicum* cell. The modified protein as defined herein may be expressed from a nucleic acid that is present in the cell. Preferably, the nucleic acid is present, e.g. stably integrated, into the genome of the cell.

In a further embodiment, the modified protein is a truncated protein. Preferably, the modified protein has at least about 60%, 70%, 75%, 80%, 81% or 81.5% sequence identity with SEQ ID NO: 1 over its full length. Preferably, the modified protein has at least about 75%, 80%, 85%, 90%, 95% 98%, 99% or 100% sequence identity when calculated over the positions corresponding to positions 1-308 of SEQ ID NO: 1 and wherein the modified protein is a truncated protein having a deletion corresponding to positions 309-378 of SEQ ID NO: 1.

Preferably the modified protein, when expressed in a plant cell, plant tissue or plant as defined herein increases resistance to Geminiviridae as compared to an otherwise identical plant cell, plant tissue or plant expressing the protein without the truncation. Preferably, the modified protein comprises an amino acid sequence having at least about 75%, 80%, 85%, 90%, 95%, 98%, 99% or about 100% sequence identity with SEQ ID NO: 5.

Preferably, the protein comprises or consists of the amino acid sequence of SEQ ID NO: 5.

In a third aspect, the invention concerns a nucleic acid comprising a sequence encoding a modified protein of the second aspect of the invention.

Preferably, said nucleic acid comprises a nucleotide sequence having at least about 75%, 80%, 85%, 90%, 95%, 98%, 99% or about 100% sequence identity with SEQ ID NO: 4. Alternatively, said nucleic acid comprises a nucleotide sequence having at least about 75%, 80%, 85%, 90%, 95%, 98%, 99% or about 100% sequence identity with SEQ ID NO: 6.

Preferably, the nucleic acid expressing the modified protein as defined herein is present in a plant cell, plant tissue or plant defined herein. The nucleic acid can be transiently introduced into the plant cell, e.g. by transient transfection of a plasmid. Alternatively or in addition, the nucleic acid can be stably present in the genome of the plant cell. As a non-limiting example, the nucleic acid may be stably integrated into the genome of the plant cell. Alternatively or in addition, the nucleic acid can be a modified endogenous nucleic acid, i.e. an endogenous nucleic acid that was modified to encode the modified protein as defined herein. Preferably, the endogenous nucleic acid is modified at one or more positions, such that the encoded protein is modified at amino acid residues corresponding to positions 69-77 of SEQ ID NO: 1. Preferably, an endogenous coding sequence having at least about 60%, 70%, 80%, 90% 95%, 98%, 99% or about 100% sequence identity with SEQ ID NO. 2 is modified to a coding sequence having at least about 60%, 70%, 80%, 90% 95%, 98%, 99% or about 100% sequence identity SEQ ID NO: 4 or SEQ ID NO: 6, preferably modified to a sequence having SEQ ID NO. 4 or SEQ ID NO. 6.

Preferably, the protein expressed from said modified coding sequence has at least about 85%, 90%, 95%, 98%, 99% or about 100% sequence identity with SEQ ID NO: 3. Alternatively, the protein expressed from said modified sequence may have at least about 85%, 90%, 95%, 98%, 99% or about 100% sequence identity with SEQ ID NO: 5.

In a further embodiment, the invention concerns a nucleic acid having at least about 75%, 80%, 85%, 90%, 95%, 98%, 99% or about 99.5% sequence identity with SEQ ID NO. 7 and wherein the sequence has a modification on a position corresponding to position 5972 or 5973 of SEQ ID NO: 7, resulting in a dysfunctional acceptor splice site prior to exon 4. SEQ ID NO. 7 is a genomic sequence comprising the coding sequence for the wild type protein as defined herein. Preferably, the guanosine at position 5973 has been modified into an adenosine. Preferably, the protein expressed from said modified sequence is a protein comprising a modification (e.g. deletion) of one or more amino acids as defined herein. Preferably, the protein expressed from said modified sequence has at least about 85%, 90%, 95%, 98%, 99% or about 100% sequence identity with SEQ ID NO: 3.

In addition, the invention pertains to a nucleic acid having at least about 75%, 80%, 85%, 90%, 95%, 98%, 99% or about 99.5% sequence identity with SEQ ID NO. 7 and wherein the sequence comprises an early stop codon as defined herein. The modified protein expressed from said sequence is preferably a truncated protein as defined herein. Preferably, the protein expressed from said modified sequence has at least about 85%, 90%, 95%, 98%, 99% or about 100% sequence identity with SEQ ID NO: 5.

In a fourth aspect, the invention pertains to a nucleic acid construct comprising the nucleic acid as defined herein. Preferably, the nucleic acid is operably linked to a transcription regulatory element for expression in a cell. Preferably, the transcription regulatory element is a promoter element. Hence in one embodiment, the nucleic acid construct comprises a nucleic acid as defined herein that is operably linked to a promoter for expression in a cell, such as a bacterial cell or a plant cell. Preferably, the nucleic acid according to the invention is operably linked to a promoter for expression in a plant cell. The term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked can mean that the DNA sequences being linked are contiguous.

In context of the present invention, the nucleic acid as defined herein is preferably linked in a functional relationship with a promoter element. The promoter for expression in plant cells can be a constitutive promoter, an inducible promoter or a tissue specific promoter. Preferably, the promoter is a constitutive promoter. The promoter for expression in plant cells is herein understood as a promoter that is active in plants or plant cells, i.e. the promoter has the general capability to drive transcription within a plant or plant cell.

The expression of the modified protein as defined herein may be controlled by an endogenous promoter, such as, but not limited to, the promoter controlling the expression of the wild-type protein as defined herein. Preferably, the promoter has at least about 70%, 75%, 80%, 85%, 90%, 95%, 98%, 99% or about 100% sequence identity with SEQ ID NO: 8.

In a fifth aspect, the invention concerns a method for generating a plant cell, plant tissue or plant having increased resistance to Geminiviridae. Preferably, the method comprises a step of reducing the expression of a wild-type protein as defined herein. Preferably, the method comprises a step of introducing the expression of a modified protein as defined herein.

In an embodiment, the method comprises the steps of
i) providing a plant cell, plant tissue or plant; and
ii) reducing the expression of a wild-type protein, wherein the protein has at least about 75% sequence identity with SEQ ID NO: 1 over its full length. Preferably, the method comprises a step of knocking out the expression of a wild-type protein.

Preferably, the method generates a plant cell, plant tissue or plant having increased resistance to at least one or more of a monopartite and/or bipartite Geminiviridae family member, preferably monopartite and/or bipartite member of the genus *Begomovirus*.

The plant cell, plant tissue or plant can be provided using any method known to the person skilled in the art. The provided plant cell, plant tissue or plant can be a wild-type cell, tissue or plant. Alternatively, the plant cell, plant tissue or plant can be or can be derived from a cultivar and/or can be or can be derived from a genetically modified cell, tissue or plant. Preferably, the provided plant cell, plant tissue or plant is a cell, tissue or plant as defined herein. Preferably the plant is a dicot, preferably selected from the group consisting *Capsicum, Solanum lycopersicum, Manihot esculenta, Gossypium*, Cucurbitaceae, *Solanum melongena, Abelmoschus esculentus* and Fabaceae. Preferably, the plant cell, tissue or plant is (or is obtainable) from a *Capsicum* plant.

Reducing or cancelling (knocking out) the expression of the wild-type protein as defined herein can be accomplished using any conventional method known in the art, including but not limited to, siRNA, epigenetic silencing and/or introducing genomic mutations. Mutations may for example be introduced in the coding region of the wild type protein and/or in regulatory elements controlling the expression of the wild type protein. Mutations can include the alteration or deletion of one or more nucleotides. A mutation cancelling the expression of the wild-type protein can constitute the deletion of at least about 50%, 75% or 100% of the coding sequence of the wild-type protein. Knocking out the expression of the wild type protein as defined herein can be accomplished using genome-editing tools known in the art, such as the CRISPR-technology, e.g. using CRISPR-Cas or CRISPR-Cpf1.

In an embodiment, the method further comprises a step of introducing the expression of a modified protein as defined herein. Preferably, the modified protein has at least about 75% sequence identity when calculated over the positions corresponding to positions 1-66 and positions 78-308 of SEQ ID NO: 1, and wherein:
a) the protein comprises a modification of one or more amino acid residues corresponding to positions 67-77 of SEQ ID NO: 1; or b) the protein is a truncated protein having a deletion corresponding to positions 309-378 of SEQ ID NO: 1.

In an embodiment, a nucleotide sequence encoding the modified protein can be introduced into a plant to introduce expression of the protein. The nucleotide sequence express- ing the modified protein as defined herein can be introduced into a plant cell using any conventional method known in the art. As a non-limiting example, this can occur by direct transformation methods, such as *Agrobacterium* transforma- tion of plant tissue, microprojectile bombardment, elec- troporation, transfection or any one of many methods known to one skilled in the art. Similarly, introducing expression of the modified protein as defined herein can be performed by introgression of the modified protein Such breeding tech- niques are well known to one skilled in the art. Direct transformation into a plant can occur by one of many techniques known to one skilled in the art and the manner selected is not critical to the practice of the invention. Methods for introducing expression vectors into plant tissue available to one skilled in the art are varied and will depend on the plant selected. Procedures for transforming a wide variety of plant species are well known and described throughout the literature.

In one embodiment the method according to the invention introduces the expression of a modified protein having at least 75% sequence identity to SEQ ID NO: 1 and compris- ing a modification of one or more amino acid residues corresponding to positions 68-76, 69-75, 70-74, preferably at positions 71-73 of SEQ ID NO: 1. One or more amino acid modifications means that the modified protein can comprises one, two, three, four, five, six, seven, eight, nine or ten amino acid modifications in the residues correspond- ing to positions 67-77 of SEQ ID NO: 1. In a preferred embodiment, the method according to the invention intro- duces the expression of a protein comprising a modification which is a deletion of one or more amino acids in a protein of interest. In a further embodiment, the method comprises introducing a protein comprising a deletion of one or more amino acid residues at positions 68-76, 69-75, 70-74, pref- erably at positions 71-73 of SEQ ID NO: 1. One or more amino acid deletions is herein understood as that the modi- fied protein can comprise one, two, three, four, five, six, seven, eight, nine or ten amino acid deletions in the residues corresponding to positions 67-77 as compared to SEQ ID NO: 1. In a preferred embodiment, the modification is a deletion of at least one, two or three amino acid residues. Preferably, the modification is the deletion of at least one amino acid residue at position 71, 72 or 73 of SEQ ID NO: 1. More preferably, the modification is the deletion of at least two amino acid residue at position 71, 72 or 73 of SEQ ID NO: 1. Even more preferred, the modification is the deletion of at least three amino acid residue at position 71, 72 or 73 of SEQ ID NO: 1.

In an embodiment, the method according to the invention comprises a step of introducing the expression of a modified protein, wherein the modified protein is a truncated protein having a deletion corresponding to positions 309-378 of SEQ ID NO: 1.

Alternatively or in addition, the expression of the modi- fied protein is introduced by modifying the endogenous coding nucleotide sequence encoding the wild-type protein. Preferably, the endogenous coding sequence has at least about 75%, 80%, 85%, 90%, 95%, 98%, 99% or about 100% sequence identity with SEQ ID NO: 2. Preferably, the endogenous nucleotide sequence is a coding sequence that is present in the genome of the plant cell. The genomic sequence can have at least about 75%, 80%, 85%, 90%, 95%, 98%, 99% or about 100% sequence identity with SEQ ID NO: 7 and can be modified to express a modified protein as defined herein.

In one embodiment, the endogenous coding sequence is modified to express a modified protein as defined herein, e.g. a protein that has at least about 75% sequence identity with SEQ ID NO: 1 over its full length, wherein the protein comprises a modification of one or more amino acid residues corresponding to positions 67-77 of SEQ ID NO: 1, and wherein the modification increases resistance to Geminiviri- dae as compared to an otherwise identical plant cell, plant tissue or plant expressing the protein without the modifica- tion.

The modification of the endogenous sequence can be a deletion and/or a modification of at least one nucleotide. For example, the endogenous coding sequence can be modified at least at one position corresponding to positions 201-231 of SEQ ID NO: 2. Alternatively or in addition at least two or three nucleotides can be modified at a position corre- sponding to positions 201-231 of SEQ ID NO: 2. As a non-limiting example, at least 3 nucleotides are deleted or subsets of 3 nucleotides are deleted. For example, at least 3 nucleotides can be deleted at a position corresponding to a position of SEQ ID NO: 2 selected from the group consisting of 201-203, 204-206, 207-209, 210-212, 213-215, 216-218, 219-221, 222-224, 225-227 and 228-231.

Alternatively or in addition, the endogenous genomic nucleotide sequence can be modified to alter a splice site, i.e. to alter the sequence of a donor and/or an acceptor site. Preferably, the modification of the splice site results in the expression of a modified protein as defined herein. As a non-limiting example, there may be a mutation at the acceptor site, preferably the modification is at the acceptor site upstream of exon 1, 2, 3, 4, 4, 5, 6, preferably upstream of exon 4.

Preferably, the mutation of a donor and/or acceptor site results in the use of an alternative donor or acceptor site. As a non-limiting example, mutation of the acceptor site upstream of exon 4 can result in the use of an acceptor site in the coding sequence of exon 4 (as exemplified in FIG. 1). The mutation of the acceptor site upstream of exon 4 preferably results in the deletion of 9 nucleotides at the 5' end of exon 4.

The mutation of a donor or acceptor site can be a deletion of a nucleotide or the modification of a nucleotide within the donor or acceptor site. As a non-limiting example, the mutation can be a modification from one nucleotide into to another nucleotide, e.g. a G-to-A transition.

Modification or deletion of one or more endogenous nucleotides can be done using any conventional means known in the art. As a non-limiting example, the modifica- tion or deletion can be performed using CRISPR-technol- ogy, e.g. using CRISP-Cas9 or CRISPR-Cpf1.

In an embodiment, the endogenous sequence is modified to express a modified protein as defined herein, e.g. a protein that has at least about 75% sequence identity when calcu- lated over the positions corresponding to positions 1-308 of SEQ ID NO: 1 and wherein the modified protein is a truncated protein having a deletion corresponding to posi- tions 309-378 of SEQ ID NO: 1, and wherein the modifi- cation increases resistance to Geminiviridae as compared to an otherwise identical plant cell, plant tissue or plant expressing the protein without the truncation.

The mutation that results in a stop codon can be intro- duced using any convention method known to the skilled person. As a non-limiting example, the mutation can be introduced using random mutagenesis. Alternatively, the mutation can be introduced using genome-editing tools, such as CRISPR-technology.

The method for generating a plant cell, plant tissue or plant having increased resistance to Geminiviridae as defined herein may further comprise a step of iii) selecting a plant cell, plant tissue or plant expressing the modified protein.

The expression of the modified protein can be determined using any conventional method known to the skilled person. Such methods include detecting the transcript (e.g. mRNA) or detecting the protein. Non-limiting examples for detecting the transcript include e.g. PCR, q-PCR and northern blotting. Non-limiting examples for detecting the presence of the modified protein includes e.g. western blotting. The method can further comprise a step of regenerating the plant tissue or plant cell into a plant.

The method can further comprise a step of, for example, producing progeny of the plant cell, plant tissue or plant expressing the modified protein as defined herein. The method can comprise a further step of producing seeds from the plant having expressing the modified protein as defined herein. The method can further comprise, for example, growing the seeds into plants having increased resistance to Geminiviridae.

The method can further comprise, for example, testing the plant, plant tissue or plant cell for having increased resistance to Geminiviridae. Methods for testing resistance to Geminiviridae include, but are not limited to infesting the plants by classical inoculation of the leaves or by white flies that carry a Geminiviridae and inspecting the plant for disease symptoms e.g. 3-8 weeks after the infestation. An additional aspect of the invention described herein pertains to seeds produced by the plant having increased resistance to Geminiviridae as defined herein.

An additional aspect of the invention described herein pertains to plants grown from the seeds or regenerated from the plant cell, comprising the protein of the invention as defined herein, the nucleic acid of the invention as defined herein and/or the construct of the invention as defined herein.

An additional aspect of the invention described herein pertains to progeny of the plant with having increased resistance to Geminiviridae as specified herein, i.e. comprising the protein of the invention as defined herein, the nucleic acid of the invention as defined herein and/or the construct of the invention as defined herein, wherein the progeny can be obtained by selfing or breeding and selection, wherein the selected progenies retain the increased resistance to Geminiviridae of the parent plant and/or retain the expression of the modified protein as described herein.

A further aspect of the invention pertains to a plant obtained or obtainable by the method as detailed herein, comprising the protein of the invention as defined herein, the nucleic acid of the invention as defined herein and/or the construct of the invention as defined herein.

In a further aspect, the invention concerns a method for increasing the resistance to Geminiviridae in a plant cell, plant tissue or plant, wherein the method comprises the steps of:

i) providing a plant cell, plant tissue or plant;
ii) reducing the expression of a wild type protein, wherein the protein has at least about 75% sequence identity with SEQ ID NO: 1 over its full length, wherein preferably the wild-type protein is not expressed.

Preferably, the resistance is increased to at least one bipartite member of the Geminiviridae family. Preferably, resistance is increased to at least one bipartite member and at least one monopartite member of the Geminiviridae family.

The method may further comprise a step iii) of introducing the expression of a modified protein having at least about 75% sequence identity when calculated over the positions corresponding to positions 1-66 and positions 78-308 of SEQ ID NO: 1 and wherein preferably a) the modified protein comprises a modification of one or more amino acid residues corresponding to positions 67-77 of SEQ ID NO: 1; or b) the modified protein is a truncated protein having a deletion corresponding to positions 309-378 of SEQ ID NO: 1, iii) selecting a plant cell, plant tissue or plant expressing the modified protein; and iv) regenerating the selected plant wherein preferably the expression of the modified protein is introduced by modifying an endogenous nucleotide sequence encoding the wild-type protein.

Preferably, the resistance to Geminiviridae is increased as compared to a control plant as defined herein.

Preferably, the Geminiviridae is at least a bipartite member of Geminiviridae family. Preferably, the Geminiviridae is a bipartite member of Geminiviridae family The method may further comprise a step of screening the plant cell, plant tissue or plant for increased resistance to Geminiviridae. Any screening method known in the art can be used for screening the plant cell, plant tissue or plant, such as, but not limited to, the methods described below in the example section.

The invention further concerns the use of a vector for increasing the resistance to Geminiviridae in a plant cell, plant tissue or plant, wherein the vector reduces or knocks out the expression of a wild type protein as defined herein. Preferably, the wild type protein has at least 75% sequence identity with SEQ ID NO: 1 over its full length.

Preferably, the vector comprises or encodes for one or more siRNAs and/or one or more miRNAs targeting the transcript of the wild type protein.

Preferably, the vector further comprises a nucleic acid as defined herein, wherein the nucleic acid comprises a sequence encoding a modified protein as defined herein. The vector preferably comprises regulatory elements to control the expression of the modified protein.

Preferably, the resistance to Geminiviridae is increased as compared to a control plant as defined herein.

Preferably, the Geminiviridae is at least a bipartite member of Geminiviridae family. Preferably, the Geminiviridae is a bipartite member of Geminiviridae family Alternatively or in addition, the vector may encode for a gRNA-CRISPR-CAS complex, wherein the complex reduces or knocks-out the expression of a wild type protein as defined herein.

The invention further concerns the use of gRNA-CRISPR-CAS complex for increasing the resistance to Geminiviridae in a plant cell, plant tissue or plant, wherein the complex reduces or knocks out the expression of a wild type protein as defined herein. Preferably, the wild type protein has at least 75% sequence identity with SEQ ID NO: 1 over its full length.

Preferably, the gRNA in the gRNA-CRISPR-CAS complex guides the CRISPR-CAS to a gene, preferably an endogenous gene, encoding a wild type protein as defined herein. Preferably, the wild type protein has at least 75% sequence identity with SEQ ID NO: 1 over its full length.

Preferably, the resistance to Geminiviridae is increased as compared to a control plant as defined herein.

Preferably, the Geminiviridae is at least a bipartite member of Geminiviridae family. Preferably, the Geminiviridae is a bipartite member of Geminiviridae family The invention further relates to the use of a modified protein as defined herein for increasing the resistance to Geminiviridae in a plant cell, plant tissue or plant. Preferably, the modified protein has at least about 75% sequence identity when calculated over the positions corresponding to positions 1-66 and positions 78-308 of SEQ ID NO: 1 and wherein preferably a) the modified protein comprises a modification of one or more amino acid residues corresponding to positions 67-77 of SEQ ID NO: 1; or b) the modified protein is a truncated protein having a deletion corresponding to positions 309-378 of SEQ ID NO: 1, Preferably, the resistance to Geminiviridae is increased as compared to a control plant as defined herein.

Preferably, the Geminiviridae is at least a bipartite member of Geminiviridae family. Preferably, the Geminiviridae is a bipartite member of Geminiviridae family The invention also pertains to plant parts and plant products derived from the plant obtained or obtainable by the method of the inventions, wherein the plant parts and/or plant products comprise the protein of the invention as defined herein, the nucleic acid of the invention as defined herein and/or the construct of the invention as defined herein. Such parts and/or products may be seed or fruit and/or products derived therefrom. Such parts, products and/or products derived therefrom may also be non-propagating material.

EXAMPLES

Method

Figure 1:
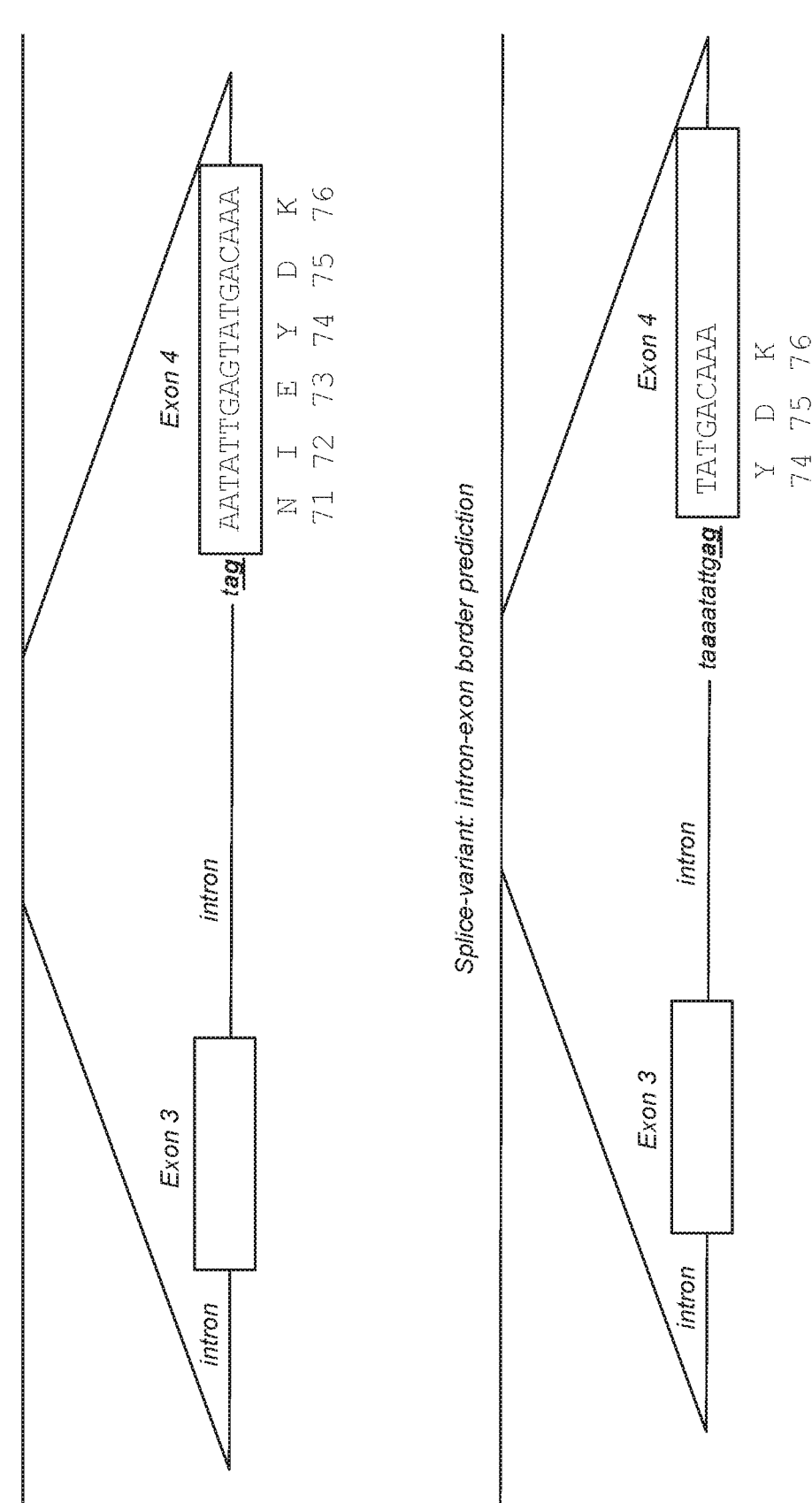
FIG. 1. Intron-exon border prediction of the dTP gene, the endogenous nucleotide sequence can be modified to alter a splice site, resulting in the use of an alternative acceptor site. The top panel shows the intron-exon border prediction of the unmodified wild-type dTP gene. The top panel recites 21 nucleotides (SEQ ID NO:27), and immediately below these nucleotides is a recitation of 6 amino acids (residues 71-76 of SEQ ID NO:2). The lower panel shows an example of a modification upstream of exon 4 wherein the modification results in the deletion of 9 nucleotides at the 5' end of exon 4. The lower panel recites 21 nucleotides (SEQ ID NO:28), and immediately below these nucleotides is a recitation of 3 amino acids (residues 74-76 of SEQ ID NO: 2).

Mutations were introduced using random mutagenesis. Maor M1 pepper plants carrying a modification in the dTP gene (SEQ ID NO: 1) were identified, of these plants two modifications were further validated. Without wishing to be bound by theory, it is believed that the modification as represented by SEQ ID NO: 3 results a splice site variation while the modification as represented by SEQ ID NO:5 introduces a STOP-codon. The validated M1 shoots of the plants carrying the modifications as represented by SEQ ID NO: 3 and SEQ ID NO:5 were propagated to seed harvest. The M1 plants were validated (by Sanger sequencing) for presence of the reported modifications. The M2 seeds of these mutant plants were harvested and grown. Homozygous M2 plants were selected for seed propagation and of those seeds the M3 plants were grown.

The Pepper Leaf Curl Virus strain M156 is a monopartite virus. The Yellow Leaf Curl Indonesian Virus (PepYLCIV) is a bipartite virus. The Huasteco Yellow Vein Virus is a bipartite virus and the Pepper Golden Mosaic Virus (PGMV) is bipartite virus.

Example 1

Pepper seeds (*Capsicum annuum*; cultivar Maor) selected for homozygous dTP mutations were sown in trays with potting soil and transplanted to Rockwool blocks. In parallel, non-mutated susceptible Maor control and additional susceptible pepper plants (commercial variety) were grown. All plants were grown in a controlled greenhouse. After 3 weeks, plants were infested with Pepper Leaf Curl Virus strain M156 (PLCV M156) using classical inoculation on leaf(s) 3 times once a week. Final evaluation for presence of virus symptoms was performed 3 weeks after the last infection. Symptoms were scored in two classes, presence of viral symptoms versus resistance (absence of symptoms) in new emerging leafs (results presented in table 2).

TABLE 2

| Percentage resistant plants to Pepper Leaf Curl Virus | | | | |
| --- | --- | --- | --- | --- |
| Seeds | Number of plants | Symptoms | Resistant | % resistant |
| dTP_Q309* (009-14) | 6 | 0 | 6 | 100 |
| dTP_Q309* (009-16) | 8 | 0 | 8 | 100 |
| dTP_A_N71-E73 (010-5) | 10 | 0 | 10 | 100 |
| dTP_A_N71-E73 (010-12) | 12 | 0 | 12 | 100 |
| Maor control | 12 | 11 | 1 | 8 |
| Susceptible variety | 6 | 6 | 0 | 0 |

Example 2

Pepper seeds (*Capsicum annuum*; cultivar Maor) selected for homozygous dTP mutations were sown in 200 well cell tray (26×26 mm) and transplanted to 50 well cell tray (50×50 mm). Plants were grown in an insect free separated controlled greenhouse. After 12 weeks, the meristem with a few leaves was grafted on test plants which stem was cut between the 2nd and 3rd true leaf. The test plants were previously infested with Pepper Yellow Leaf Curl Indonesian Virus (PepYLCIV). Symptoms were evaluated two months after successful grafting. Symptoms were scored by visual inspection in two classes, presence versus absence of viral symptoms in the new emerging leafs and are presented in table 3.

TABLE 3

Symptom free plants when infected
Pepper Yellow Leaf Curl Virus

| Seeds | Symptoms | Resistant |
|---|---|---|
| dTP_Q309* (009-14) | 0 | 1 |
| dTP_Δ_N71-E73 (010-5) | 0 | 1 |
| dTP_Δ_N71-E73 (010-12) | 0 | 1 |
| Maor control | 3 | 0 |

Furthermore, virus titers were determined by PCR-based detection methods. The relative titer of PepYLCIV was determined using a qPCR primer specific for PepYLCIV. The level of PepYLCIV in susceptible wild-type Maor background of the mutant plants was set to 100% and subsequently compared to the virus titers of infested plants expressing SEQ ID NO: 3 or SEQ ID NO:5. The results are presented in table 4.

TABLE 4

PepYLCIV titers.

| Plant genotype | Relative titer PepYLCIV |
|---|---|
| dTP_Q309* (SEQ ID NO: 5) | 1.37% |
| dTP_Δ_N71-E73 (SEQ ID NO: 3) | 2.33% |
| Maor control (SEQ ID NO: 1) | 100% |

Example 3

The effect of the modifications of SEQ ID NO: 3 and SEQ ID NO:5 on germination were analyzed. At the M2 stage, any modification in the dTP gene is expected to segregate in a Mendelian fashion (i.e. it is expected that 25% of all plants to carry the mutant allele in a homozygous state). However, for the plants carrying the modification as represented by SEQ ID NO: 5 a skewed segregation was observed: only 15.7% of the germinated plants were homozygous for the modification as represented by SEQ ID NO: 5. Homozygous mutant M2 plants were grown to obtain selfed M3 seed. Sowing of these M3 seeds resulted in very few germinating seedlings (~4%). In contrast, segregation at the M2 stage for the plants carrying SEQ ID NO:3 was normal with an observed 27.5% of homozygous mutant alleles. M3 seed germination percentage is 48%. Hence an allele was identified that provides geminivirus resistance, but that is not hampered by extremely low germination percentage. The results are summarized in table 5.

TABLE 5

Germination percentages

| | Germination | |
|---|---|---|
| | M2 | M3 |
| SEQ ID NO: 3 | 27.5% | 48% |
| SEQ ID NO: 5 | 16% | 4% |
| Expected | 25% | 50% |

Example 4

Pepper seeds (*Capsicum annuum*; cultivar Maor) selected for homozygous dTP mutations were sown in trays with potting soil and transplanted to soil. In parallel, non-mutated Maor was grown as control. All plants were grown in a controlled greenhouse. After 12 weeks, plants were infested by white flies that carry the bipartite Pepper Huasteco Yellow Vein Virus (PHYVV). Infestation by viruliferous whiteflies has been described by Hutton et al (Hortscience 47 (3): 324-327. 2012). In brief, seedlings 3 weeks past the cotyledon stage (two to three leaves) were exposed to viruliferous whiteflies for 2 weeks in growth chambers. After inoculation, the whiteflies were killed by treating plants with an insecticidal soap and with Admire (imidacloprid), and the plants were transplanted to the field/Greenhouse. Final evaluation for presence of virus symptoms was performed 40 days after the last infection. Plants were scored in 3 classes, Resistant (R), Intermediate (I) or susceptible(S). Samples of symptomless plants were further evaluated for presence of PHYVV using conventional PCR. Results are presented in table 6.

TABLE 6

| Seeds | Number of plants | Susceptible | Intermediate | Resistant |
|---|---|---|---|---|
| dTP_Δ_N71-E73 (010-16) | 5 | 0 | 2 | 3 |
| dTP_Δ_N71-E73 (010-16) | 4 | 1 | 0 | 3 |
| Maor control | 7 | 7 | 0 | 0 |

Example 5

Pepper seeds (*Capsicum annuum*; cultivar Maor) selected for homozygous dTP mutations were sown in trays with potting soil and transplanted to pots with potting soil. In parallel, non-mutated susceptible control Maor, additional susceptible controls Monet and Yolo Wonder and a resistant control were grown. All plants were grown in a non-controlled greenhouse. Plants were infested by white flies that carry the bipartite Pepper Huasteco Yellow Vein Virus (PHYVV) and the Pepper Golden Mosaic Virus (PGMV) as described in example 4. Final evaluation for presence of virus symptoms was performed 40 days after the last infection. Plants were scored in 4 classes.

TABLE 7

| Seeds | Number of plants | Symptoms | Intermediate | Resistant | % resistant |
|---|---|---|---|---|---|
| dTP_Δ_N71-E73 | 19 | 4 | 12 | 3 | 15.8 |
| dTP_Q309* | 2 | 1 | 0 | 1 | 50 |
| Maor control | 32 | 8 | 24 | 0 | 0 |
| Susceptible control (Monet) | 81 | 13 | 64 | 4 | 4.9 |
| Susceptible control (Yolo wonder) | 16 | 11 | 5 | 0 | 0 |
| Control (Resistant) | 57 | 0 | 16 | 41 | 71.9 |

Example 6

In order to test the germination percentage of unmutated and dTP mutant variants, mutant plants (homozygous for SEQ ID NO: 4 or SEQ ID NO:6) are crossed to unmutagenized Maor plants. The corresponding F1 (heterozygous) are subsequently self-fertilized to obtain F2 seeds, which segregate for the intended variants comprising SEQ ID NO: 3 or SEQ ID NO: 5. 40 segregated F2 seeds are sown and the germination percentage is determined. DNA from germinated seedlings is extracted and the ratio between homozygous dTP mutation, heterozygous and homozygous WT is determined using standard genotyping techniques. In comparison to plants comprising SEQ ID NO: 4 where a normal segregation of 1:2:1 is expected, a skewed segregation can be observed in the germinated F2 plants derived from seeds comprising SEQ ID NO:6, wherein segregation is skewed in favor of heterozygocity of wild-type alleles of dTP instead of homozygous mutant alleles, indicating that a truncated plant expressing a protein as represented by SEQ ID NO:5 has unwanted pleiotropic effects resulting in decreased germination percentage. These unwanted effects will not be observed in mutant plants homozygous for SEQ ID NO: 3.

Example 7

In order to test if impaired expression of the dTP gene or alterations of the protein leads to increased resistance to geminiviruses in *Arabidopsis* the following experiment was executed. Seeds of *Arabidopsis thaliana* were obtained from the Nottingham *Arabidopsis* Stock Centre (NASC) that carry a T-DNA insertion in the dTP gene (AT4G27650). Two SALK T-DNA insertion lines were obtained: SALK_121667.17.55x and SALK_124403.21.45x. Plants homozygous for a T-DNA insertion in the dTP gene were selected and grown in potting soil for 3-weeks. Subsequently, the plants were infected with *Agrobacterium tume-*

Figure 2:
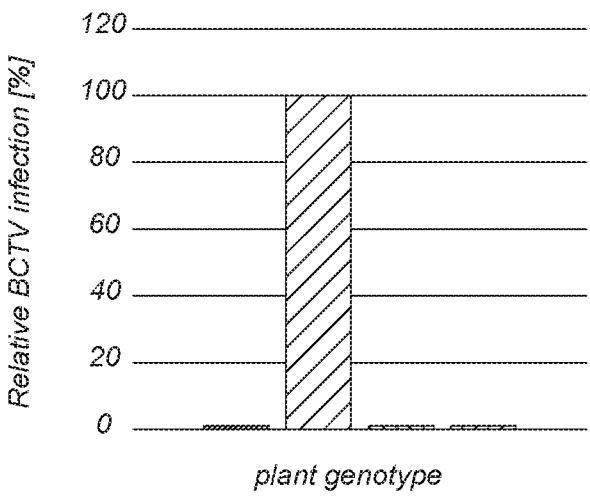
FIG. 2. Beet Curly Top Virus susceptibility. Relative titer of BCTV in Col-0 and SALK_124403.21.45x plants that are either uninfected or infected with BCTV. No virus replication takes place in the T-DNA plants.

*faciens* expressing Beet curly top virus (BCTV) from a binary plasmid. The *Agrobacterium* was grown overnight and applied to the petiole of several leaves of each *Arabidopsis* plant using an small gauge (22-25) syringe. This monopartite geminivirus has been shown to infect a large range of (crop) plants, including *Arabidopsis*. Disease symptoms (curling of the leaves) occurred within 10 days after infection, but to determine the virus titer in wild-type (Col-0) and T-DNA *Arabidopsis* plants QPCR was performed on DNA isolated from infected and uninfected plant material. The following primers were used to detect BTCV: BCTV1: CTACACGAAGATGGGCAACCT (SEQ ID NO: 9) and BCTV2: TGACGTCGGAGCTGGATTTAG (SEQ ID NO: 10) (described in Luna et al., 2017—Journal of General Virology 2017; 98:2607-2614). FIG. 2 indicates that BCTV infection in wild-type *Arabidopsis* (Col-0) results in viral replication and disease. In contrast, BCTV infection of T-DNA insertion lines in the dTP gene did not cause viral replication, nor disease.

Subsequent experiments aimed at proving that homologous proteins from other crop plant species have a similar function in resistance to Geminiviruses. To this end the crop homologs were identified (Table 8).

TABLE 8

| Amino acid identity matrix of the dTP protein between different plant species. | | | | | | | | | |
|---|---|---|---|---|---|---|---|---|
| | *Arabidopsis* | Pepper | *S. lyc* | Zucchini | Cassava | Cotton | Cotton | Soybean | Soybean |
| *Arabidopsis* | 100.00 | 79.63 | 80.69 | 81.64 | 81.22 | 81.43 | 81.96 | 80.69 | 80.69 |
| Pepper | 79.63 | 100.00 | 94.97 | 82.49 | 82.01 | 81.70 | 82.76 | 80.69 | 80.69 |
| *S. lycopersicum* | 80.69 | 94.97 | 100.00 | 82.49 | 82.28 | 81.70 | 82.76 | 81.48 | 81.48 |
| Zucchini | 81.64 | 82.49 | 82.49 | 100.00 | 85.03 | 83.57 | 83.85 | 83.33 | 83.33 |
| Cassava | 81.22 | 82.01 | 82.28 | 85.03 | 100.00 | 87.27 | 87.53 | 85.19 | 85.19 |
| Cotton | 81.43 | 81.70 | 81.70 | 83.57 | 87.27 | 100.00 | 98.41 | 85.15 | 85.15 |
| Cotton | 81.96 | 82.76 | 82.76 | 83.85 | 87.53 | 98.41 | 100.0 | 86.21 | 86.21 |
| Soybean | 80.69 | 80.69 | 81.48 | 83.33 | 85.19 | 85.15 | 86.21 | 100.00 | 100.00 |
| Soybean | 80.69 | 80.69 | 81.48 | 83.33 | 85.19 | 85.15 | 86.21 | 100.00 | 100.00 |

Figure 3:
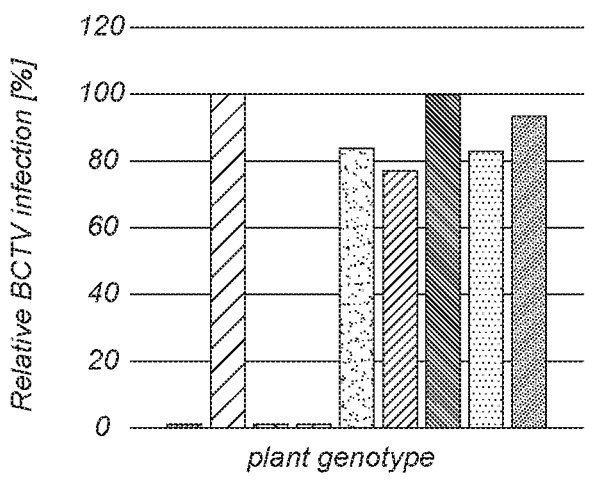
FIG. 3. Beet Curly Top Virus susceptibility by dTP complementation. Relative titer of BCTV in Col-0 and SALK_124403.21.45x plants that are either uninfected or infected with BCTV.

Upon identification, these homologous genes were cloned and transformed into the *Arabidopsis* T-DNA lines. Expression of the coding sequence was driven by the 35S promoter. Transgenic *Arabidopsis* lines over-expressing the crop homologs of dTP were subjected to BCTV infection and compared to the T-DNA insertion line in dTP expressing a 35S: GUS construct. FIG. 3 shows the relative virus titer of the complementation lines. Lines that show susceptibility to BCTV indicate that the particular crop homolog expressed in these lines is able to complement the dTP function and hence can be modified to create plants that are resistant to geminiviruses in these crops. In particular, FIG. 3 shows complementation for dTP from cassava, zucchini, pepper, *Arabidopsis* and cotton. Clearly, no virus replication takes place in the T-DNA plants. The T-DNA lines that were complemented with crop homologs of dTP showed increased susceptibility indicating that these gene/proteins have similar functions in their respective crop plant.

TABLE 9

| SEQ ID NOs dTP nucleotide and amino acid sequences | | |
|---|---|---|
| | Amino acid sequence (SEQ ID NO) | Nucleotide sequence (SEQ ID NO) |
| Pepper | 1 | 2 |
| Zucchini | 11 | 19 |
| Cassava | 12 | 20 |
| Cotton | 13 | 21 |
| Cotton | 14 | 22 |
| Soybean | 15 | 23 |
| Soybean | 16 | 24 |
| *Arabidopsis* | 17 | 25 |
| *S. lycopersicum* | 18 | 26 |

The invention claimed is:

1. A method for producing a *Capsicum* plant cell, plant tissue or plant resistant to at least one bipartite member of the Geminiviridae family selected from the group consisting of Yellow Leaf Curl Indonesian Virus (PepYLCIV), Huatesco Yellow Vein Virus (PHYVV), and Pepper Golden Mosaic Virus (PGMV), the method comprising:

(i) abolishing the expression of an endogenous dTP protein encoded by the genome of the *Capsicum* plant in the plant cell, plant tissue or plant, wherein the endogenous dTP protein comprises the amino acid sequence of SEQ ID NO: 1 or a homologue thereof having at least 99% sequence identity to SEQ ID NO: 1 over its full length, wherein the expression of the endogenous protein is abolished by modifying at least one nucleotide in the nucleotide sequence encoding the endogenous dTP protein resulting in a sequence encoding a non-functional dTP protein; and (ii) screening the plant cell, plant tissue or plant for resistance to at least one of PepYLCIV, PHYVV, and PGMV.

2. The method according to claim 1, wherein the method further comprises regenerating a plant from said plant cell and/or plant tissue wherein the regenerated plant expresses said non-functional dTP protein.

3. The method according to claim 1, wherein the modifying or deleting results in the expression of a modified protein having the amino acid sequence of SEQ ID NO: 3 or 5.

4. The method according to claim 3, further comprising selecting a plant cell, plant tissue or plant expressing the modified protein.

5. The method of claim 1, wherein the *Capsicum* plant cell, plant tissue or plant is *Capsicum annuum*.

6. The method of claim 1, wherein the protein comprises the amino acid sequence of SEQ ID NO: 1.

*    *    *    *    *

SEQUENCE LISTING

<160> NUMBER OF SEQ ID NOS: 28

<210> SEQ ID NO 1
<211> LENGTH: 378
<212> TYPE: PRT
<213> ORGANISM: Capsicum annuum

<400> SEQUENCE: 1

Met Lys Ile Val Arg Lys Asp Leu Val Pro Asp Gly Pro Gly Ser Val
1               5                   10                  15

Lys Ile Ile Pro Glu Glu Ala Asp Asp Met Trp Val Ala Tyr Asn Leu
                20                  25                  30

Ile Ala Glu Gly Asp Thr Val Leu Ala Val Thr Val Arg Lys Val Leu
            35                  40                  45

Arg Glu Ala Ala Ser Gly Gly Arg Asp Ala Glu Arg Val Lys Leu Lys
        50                  55                  60

Leu Glu Ile Lys Val Glu Asn Ile Glu Tyr Asp Lys Glu Gly Ser Ala
65                  70                  75                  80

Leu Arg Ile Arg Gly Lys Asn Ile Leu Glu Asn Glu His Val Lys Ile
                85                  90                  95

Gly Ala Phe His Thr Leu Glu Ile Glu Pro His Arg Pro Phe Val Leu
                100                 105                 110

Arg Lys Val Val Trp Asp Ser Leu Ala Arg Glu Val Leu Arg Gln Ala
                115                 120                 125

Ala Asp Pro Ser Val Ser Ala Asp Leu Ala Val Val Leu Met Gln Glu
        130                 135                 140

Gly Leu Ala His Ile Leu Leu Ile Gly Lys Ser Leu Thr Ile Thr Arg
145                 150                 155                 160

Ser Arg Ile Glu Thr Ser Ile Pro Arg Lys His Gly Pro Ala Ile Ala
                165                 170                 175

Gly Tyr Asp Lys Ala Leu Asn Lys Phe Phe Gly Asn Val Leu Gln Ala
                180                 185                 190

Phe Val Arg His Val Asp Phe Lys Val Val Arg Cys Ala Val Ile Ala
                195                 200                 205

Ser Pro Gly Phe Thr Lys Asp Gln Phe His Arg His Leu Leu Leu Glu
        210                 215                 220

Ala Glu Arg Lys Gln Leu Arg Pro Ile Ile Glu Asn Lys Ser Arg Ile
225                 230                 235                 240

Leu Leu Val His Thr Thr Ser Gly Tyr Lys His Ser Leu Lys Glu Val
                245                 250                 255

Leu Asp Ala Pro Asn Val Met Asn Met Ile Lys Asp Thr Lys Ala Ala
                260                 265                 270

Lys Glu Val Gln Ala Leu Lys Glu Phe Phe Asn Met Leu Ser Asn Asp
        275                 280                 285

Pro Asp Arg Ala Cys Tyr Gly Pro Lys His Val Glu Val Ala His Glu
        290                 295                 300

Arg Met Ala Ile Gln Thr Leu Leu Ile Thr Asp Glu Leu Phe Arg Ser
305                 310                 315                 320

Ser Asp Val Glu Thr Arg Lys Lys Tyr Ala Asn Leu Val Asp Ser Val
                325                 330                 335

Lys Asp Ser Gly Gly Thr Ala Leu Ile Phe Ser Ser Met His Val Ser
                340                 345                 350

Gly Glu Gln Leu Thr Gln Leu Thr Gly Ile Ala Ala Ile Leu Arg Phe
        355                 360                 365

-continued

```
Pro Leu Pro Glu Leu Glu Asp Ile Glu Met
    370                 375

<210> SEQ ID NO 2
<211> LENGTH: 1137
<212> TYPE: DNA
<213> ORGANISM: Capsicum annuum

<400> SEQUENCE: 2
atgaaaattg ttcgaaaaga ccttgttcct gatggccctg gtagtgtcaa gataattcca        60
gaggaagcag atgatatgtg ggttgcttat aatttgatag ctgaaggtga tactgttttg       120
gctgttactg tcaggaaggt cctaagggaa gctgcttctg gaggaagaga tgctgaacga       180
gtgaaactga aattggaaat caaagttgag aatattgagt atgacaaaga aggttctgcc       240
ttgcgtattc gtgggaagaa tatcctggag aatgaacatg taaagatagg cgcttttcac       300
actctggaaa ttgagccaca cagacctttt gtgctaagaa aggtggtctg ggactcactg       360
gcacgagagg ttcttcgtca agctgctgat ccttctgtaa gtgctgatct ggctgttgtt       420
ctgatgcaag aaggattggc acacatactt cttattggta aaagcttgac tattactcgt       480
tctcgtatag agacttctat accacgcaag catggaccag caattgcagg ttatgataag       540
gcgttaaata agttctttgg caatgttcta caggcctttg tcaggcatgt tgatttcaaa       600
gtagttcgct gtgctgtgat tgcaagtcca ggattcacca aggatcaatt tcatcgtcac       660
ctgttgttag aagccgagag gaagcagcta agacctataa tagaaaataa atcacgcata       720
cttcttgtcc atacaacctc aggatacaaa catagtttga agaggttct ggatgcccca        780 aacgtaatga atatgataaa agatacaaaa gctgccaaag aggttcaagc tctaaaggaa       840
tttttcaaca tgctttcaaa tgatcctgat cgtgcatgct atggaccaaa gcatgttgaa       900
gttgctcacg agcgaatggc tatccagaca cttctcatta ccgacgagct ctttaggagt       960
tctgatgtag aaacgaggaa aaagtatgcc aatctggttg attcagtcaa ggattccggt      1020
ggtactgcac tcattttctc atcaatgcac gtttcaggag aacaactgac acagctaacc      1080
ggcattgctg caatccttcg ttttcctttg ccggagctgg aagacattga gatgtga        1137

<210> SEQ ID NO 3
<211> LENGTH: 375
<212> TYPE: PRT
<213> ORGANISM: artificial sequence
<220> FEATURE:
<223> OTHER INFORMATION: Artificial modification in which residues at
      positions 70, 71, and 72 are deleted, relative to SEQ ID NO:1

<400> SEQUENCE: 3

Met Lys Ile Val Arg Lys Asp Leu Val Pro Asp Gly Pro Gly Ser Val
1               5                   10                  15

Lys Ile Ile Pro Glu Glu Ala Asp Asp Met Trp Val Ala Tyr Asn Leu
            20                  25                  30

Ile Ala Glu Gly Asp Thr Val Leu Ala Val Thr Val Arg Lys Val Leu
        35                  40                  45

Arg Glu Ala Ala Ser Gly Gly Arg Asp Ala Glu Arg Val Lys Leu Lys
    50                  55                  60

Leu Glu Ile Lys Val Glu Tyr Asp Lys Glu Gly Ser Ala Leu Arg Ile
65                  70                  75                  80

Arg Gly Lys Asn Ile Leu Glu Asn Glu His Val Lys Ile Gly Ala Phe
                85                  90                  95

His Thr Leu Glu Ile Glu Pro His Arg Pro Phe Val Leu Arg Lys Val
```

-continued

```
                100                 105                 110
Val Trp Asp Ser Leu Ala Arg Glu Val Leu Arg Gln Ala Ala Asp Pro
        115                 120                 125
Ser Val Ser Ala Asp Leu Ala Val Val Leu Met Gln Glu Gly Leu Ala
    130                 135                 140
His Ile Leu Leu Ile Gly Lys Ser Leu Thr Ile Thr Arg Ser Arg Ile
145                 150                 155                 160
Glu Thr Ser Ile Pro Arg Lys His Gly Pro Ala Ile Ala Gly Tyr Asp
                165                 170                 175
Lys Ala Leu Asn Lys Phe Phe Gly Asn Val Leu Gln Ala Phe Val Arg
            180                 185                 190
His Val Asp Phe Lys Val Val Arg Cys Ala Val Ile Ala Ser Pro Gly
            195                 200                 205
Phe Thr Lys Asp Gln Phe His Arg His Leu Leu Leu Glu Ala Glu Arg
        210                 215                 220
Lys Gln Leu Arg Pro Ile Ile Glu Asn Lys Ser Arg Ile Leu Leu Val
225                 230                 235                 240
His Thr Thr Ser Gly Tyr Lys His Ser Leu Lys Glu Val Leu Asp Ala
                245                 250                 255
Pro Asn Val Met Asn Met Ile Lys Asp Thr Lys Ala Ala Lys Glu Val
                260                 265                 270
Gln Ala Leu Lys Glu Phe Phe Asn Met Leu Ser Asn Asp Pro Asp Arg
        275                 280                 285
Ala Cys Tyr Gly Pro Lys His Val Glu Val Ala His Glu Arg Met Ala
    290                 295                 300
Ile Gln Thr Leu Leu Ile Thr Asp Glu Leu Phe Arg Ser Ser Asp Val
305                 310                 315                 320
Glu Thr Arg Lys Lys Tyr Ala Asn Leu Val Asp Ser Val Lys Asp Ser
                325                 330                 335
Gly Gly Thr Ala Leu Ile Phe Ser Ser Met His Val Ser Gly Glu Gln
            340                 345                 350
Leu Thr Gln Leu Thr Gly Ile Ala Ala Ile Leu Arg Phe Pro Leu Pro
        355                 360                 365
Glu Leu Glu Asp Ile Glu Met
    370                 375
```

```
<210> SEQ ID NO 4
<211> LENGTH: 1128
<212> TYPE: DNA
<213> ORGANISM: artificial sequence
<220> FEATURE:
<223> OTHER INFORMATION: Artificially modified sequence in which
      nucleotides at positions 206-214 are deleted, relative to SEQ ID
      NO:2

<400> SEQUENCE: 4
atgaaaattg ttcgaaaaga ccttgttcct gatggccctg gtagtgtcaa gataattcca        60
gaggaagcag atgatatgtg ggttgcttat aatttgatag ctgaaggtga tactgttttg       120
gctgttactg tcaggaaggt cctaagggaa gctgcttctg gaggaagaga tgctgaacga       180
gtgaaactga aattggaaat caaagttgag tatgacaaag aaggttctgc cttgcgtatt       240
cgtgggaaga atatcctgga gaatgaacat gtaaagatag cgcttttca cactctggaa        300 attgagccac acagaccttt tgtgctaaga aaggtggtct gggactcact ggcacgagag       360
gttcttcgtc aagctgctga tccttctgta agtgctgatc tggctgttgt tctgatgcaa       420
```

-continued

```
gaaggattgg cacacatact tcttattggt aaaagcttga ctattactcg ttctcgtata    480
gagacttcta taccacgcaa gcatggacca gcaattgcag gttatgataa ggcgttaaat    540
aagttctttg gcaatgttct acaggccttt gtcaggcatg ttgatttcaa agtagttcgc    600
tgtgctgtga ttgcaagtcc aggattcacc aaggatcaat ttcatcgtca cctgttgtta    660
gaagccgaga ggaagcagct aagacctata atagaaaata aatcacgcat acttcttgtc    720
catacaacct caggatacaa acatagtttg aaagaggttc tggatgcccc aaacgtaatg    780
aatatgataa aagatacaaa agctgccaaa gaggttcaag ctctaaagga atttttcaac    840
atgctttcaa atgatcctga tcgtgcatgc tatggaccaa agcatgttga agttgctcac    900
gagcgaatgg ctatccagac acttctcatt accgacgagc tctttaggag ttctgatgta    960
gaaacgagga aaaagtatgc caatctggtt gattcagtca aggattccgg tggtactgca   1020
ctcattttct catcaatgca cgtttcagga gaacaactga cacagctaac cggcattgct   1080
gcaatccttc gttttccttt gccggagctg gaagacattg agatgtga               1128
```

<210> SEQ ID NO 5
<211> LENGTH: 308
<212> TYPE: PRT
<213> ORGANISM: artificial sequence
<220> FEATURE:
<223> OTHER INFORMATION: Artificial modification in which residues at
      positions 309-378 are deleted, relative to SEQ ID NO:1

<400> SEQUENCE: 5

```
Met Lys Ile Val Arg Lys Asp Leu Val Pro Asp Gly Pro Gly Ser Val
1               5                   10                  15

Lys Ile Ile Pro Glu Glu Ala Asp Asp Met Trp Val Ala Tyr Asn Leu
            20                  25                  30

Ile Ala Glu Gly Asp Thr Val Leu Ala Val Thr Val Arg Lys Val Leu
        35                  40                  45

Arg Glu Ala Ala Ser Gly Gly Arg Asp Ala Glu Arg Val Lys Leu Lys
    50                  55                  60

Leu Glu Ile Lys Val Glu Asn Ile Glu Tyr Asp Lys Glu Gly Ser Ala
65                  70                  75                  80

Leu Arg Ile Arg Gly Lys Asn Ile Leu Glu Asn Glu His Val Lys Ile
            85                  90                  95

Gly Ala Phe His Thr Leu Glu Ile Glu Pro His Arg Pro Phe Val Leu
            100                 105                 110

Arg Lys Val Val Trp Asp Ser Leu Ala Arg Glu Val Leu Arg Gln Ala
        115                 120                 125

Ala Asp Pro Ser Val Ser Ala Asp Leu Ala Val Val Leu Met Gln Glu
    130                 135                 140

Gly Leu Ala His Ile Leu Leu Ile Gly Lys Ser Leu Thr Ile Thr Arg
145                 150                 155                 160

Ser Arg Ile Glu Thr Ser Ile Pro Arg Lys His Gly Pro Ala Ile Ala
            165                 170                 175

Gly Tyr Asp Lys Ala Leu Asn Lys Phe Phe Gly Asn Val Leu Gln Ala
            180                 185                 190

Phe Val Arg His Val Asp Phe Lys Val Val Arg Cys Ala Val Ile Ala
            195                 200                 205

Ser Pro Gly Phe Thr Lys Asp Gln Phe His Arg His Leu Leu Leu Glu
    210                 215                 220

Ala Glu Arg Lys Gln Leu Arg Pro Ile Ile Glu Asn Lys Ser Arg Ile
225                 230                 235                 240
```

-continued

```
Leu Leu Val His Thr Thr Ser Gly Tyr Lys His Ser Leu Lys Glu Val
            245                 250                 255

Leu Asp Ala Pro Asn Val Met Asn Met Ile Lys Asp Thr Lys Ala Ala
            260                 265                 270

Lys Glu Val Gln Ala Leu Lys Glu Phe Phe Asn Met Leu Ser Asn Asp
        275                 280                 285

Pro Asp Arg Ala Cys Tyr Gly Pro Lys His Val Glu Val Ala His Glu
    290                 295                 300

Arg Met Ala Ile
305

<210> SEQ ID NO 6
<211> LENGTH: 927
<212> TYPE: DNA
<213> ORGANISM: artificial sequence
<220> FEATURE:
<223> OTHER INFORMATION: Artificially modified sequence in which
      nucleotide C925 replaced with a T, and nucleotides at positions
      928-1137 are deleted; relative to SEQ ID NO:2

<400> SEQUENCE: 6
atgaaaattg ttcgaaaaga ccttgttcct gatggccctg gtagtgtcaa gataattcca        60
gaggaagcag atgatatgtg ggttgcttat aatttgatag ctgaaggtga tactgttttg       120
gctgttactg tcaggaaggt cctaagggaa gctgcttctg gaggaagaga tgctgaacga       180
gtgaaactga aattggaaat caaagttgag aatattgagt atgacaaaga aggttctgcc       240
ttgcgtattc gtgggaagaa tatcctggag aatgaacatg taaagatagg cgcttttcac       300
actctggaaa ttgagccaca cagacctttt gtgctaagaa aggtggtctg ggactcactg       360
gcacgagagg ttcttcgtca agctgctgat ccttctgtaa gtgctgatct ggctgttgtt       420
ctgatgcaag aaggattggc acacatactt cttattggta aaagcttgac tattactcgt       480
tctcgtatag agacttctat accacgcaag catggaccag caattgcagg ttatgataag       540
gcgttaaata gttctttgg caatgttcta caggcctttg tcaggcatgt tgatttcaaa        600
gtagttcgct gtgctgtgat tgcaagtcca ggattcacca aggatcaatt tcatcgtcac       660
ctgttgttag aagccgagag gaagcagcta agacctataa tagaaaataa atcacgcata       720
cttcttgtcc atacaacctc aggatacaaa catagtttga aagaggttct ggatgcccca       780
aacgtaatga atatgataaa agatacaaaa gctgccaaag aggttcaagc tctaaaggaa       840
tttttcaaca tgctttcaaa tgatcctgat cgtgcatgct atggaccaaa gcatgttgaa       900
gttgctcacg agcgaatggc tatctag                                          927

<210> SEQ ID NO 7
<211> LENGTH: 9614
<212> TYPE: DNA
<213> ORGANISM: Capsicum annuum

<400> SEQUENCE: 7
atgaaaattg ttcgaaaaga ccttgttcct gatggccctg gtagtgtcaa ggtaacaaaa        60
aaatattttc tttaattgtt tttatatcat taaatttgag ttattatctt gatattttaa       120
ttacccagaa aaagaaaatg gttaaattat tctgggtatt ttttatttta ttttttaatc       180
ttgtaaaata ttttgtatca tttaatttga gttattttct tgatattttg atgacccaga       240
agaggaaaat tgttaaatta atctgggtat tttttatttt ttcattaaat agataattcc       300
agaggaagca gatgatatgt gggttgctta taatttgata gctgaaggtg atactgtttt       360
```

-continued

```
ggctgttact gtcaggtatt aaaatttcgt tttatttcat ataatttttgc gtttttaattt     420 gtttgtctta ttttttccttt tagtccgttt attgaagagt gtatctttac ttgttttttgg     480 tgattctttta attcgaactt tccaggtggc ttgtttaaaa ccacaagatt aaatgatatg     540
ttggtacttt ccacgtatct tttagtttaa aacgtatctt ttagtttaaa acgataagat     600
tcaaaagtct ttttttactt tcttaaacta tgtgtcaagt caaaatcaga gtgagtaatt     660
tattcgtgtg aaggggaaat tttccaaaca caagatgtgt aaaaaaggta aagaatttgt     720
cgaaaaatat gtttttttttt tctataagaa gcaatgccgt aggtgctaca agaatttact     780
aaacatgtat aatttgatca tgaagatgaa atctttatgt ccttaacatg aatgtcattt     840
gctaattagg tccaaattga gtgcattctg aagcttgaag ggcccttta taatttgatc     900 atgaaagatg gaatctttat gttgaatgaa ttcttgaata cgagcgttgc tttctaatta     960
ggtcccgatt cagttcattc gaaatcttga agctcccttt tatatttttga ccatgagaga    1020 tggaatcttt atgttgaatg aattcttgaa tacgagtgtt gctttctaat taggtcccga    1080
ttcagttcat tcgaaatctt gaagctccct tttataattt gaccatgaaa gatggaatct    1140
ttatgttgaa tgaattttcg aatacgagtg ttgcttgcta attaggtccc gattcagttc    1200
attcgaaatc ttgaagctcc cttttataat ttgaccatgg aagatggaat ctttatgttg    1260
aatgaattct tgaatatgag tgtcgcttgc taagaagaaa gtggagacta agaaggggac    1320
gtatgctaag ttggttgaga gtaaagatga agaggataag cggctaaata gggaggagta    1380
caagttagct aggagagagg ccaagttagc agttacggct gctaagacgg cagcgtttga    1440
gagcttgtat gcggggttag aggagagagg cggggaaaaa aggttgtata agcttgctaa    1500
ggctagggag aggaagggtc gtaaccttga tcaagtgaag tgtattaagg gggagaatgg    1560
tagtgtgctg gtggaggacg tgcatattaa gagaagatga cagtcgtatt ttcatagact    1620
cttgaatgat gaggggggaca atgacattgt gttaggggag ctggagcact ctgagggggtg    1680 tcgtgatttc agctattgta ggcgttttaa ggtggaggag gtccgggagg ctattcacag    1740
gatgcgaagg ggtagggcga cgaggcctga cgagattcct gtggatttttt gaaagtgtat    1800 tggcggtgct ggtttaaggt ggttgactga gttgtttaat gacatctttta agactgcgaa    1860 aatgcccgag gcttggagat ggagtatcat gattccttta tataagaaca agggtgacat    1920
ccagagttgc aacaactata ggggtattaa gttgttgagt cacactatga agatttggga    1980
gagagtggtc gagcggaggt tgaggatgat agtgtctatt tcggagaatt agtttggatt    2040
tatgctcggg tcctcgacga ctgaggcaat tcacctgatg cggagactgg tggagcagta    2100
tagagaaagg aagaaggacc ttcacatggt gtttatcaac ttggagaagg catacgacaa    2160
agtctctaga gaggttcttt ggagatgctt ggaggtgagt gggggtcccg gtggcgtaca    2220
tcagatcgat taaggacgtg tatgacggag caaagactca ggtgaggatg gcgggaggag    2280
attcagagca ttcagggtgg catcagggat cgacgcttag cccgtttctg tttgtgttgg    2340
tgatggatgt gttgacgcgg cggcgtattc aaggaaaggt gccttggttt atgttttttg    2400
cagatgatgt agtattaatt ttcgagacgc agggaggtgt gaatgataaa ttggaggttt    2460
ggagacaaac ctttgagtct aaagggttca ggctgagtag gagcaagacc gagtatatgg    2520
aatgcaagtt taaggacttg agacaggagg acgaggtggt agtaaggttg ggttcccagg    2580
ttgtgtgtaa gagggatagt tttaagtatt tcgggtcgat gattcagggg aatggtgaga    2640
ttgatgagga tatctcccat cgtattgggg caggatggat gaagtggagg ctcgcctagg    2700
```

-continued

```
gagtattgtg tgataagaag gtgccgccca aacttaaagg taaattttat agagtggtag      2760
tcctttcggc catgctgtat gaagcggagt gttggccagt caagaactcc catattcaaa      2820
aactgaaggt ggcggaaatg cggatgttgc gttggatgtg tgggcttact aggggtgata      2880
ggtttaggaa tgaaactgtc cgagagaagg ttggtgtggc ttcggtggag gacaagatgc      2940
gggaagttcg ggtgagatgg ttcgggcatg tgatgaggag gggcacggat gccctagttc      3000
gtagatgtga gaggttagct ttggatggtt ttaggcgggg taggggtagg ctgaagaaat      3060
attggagaga ggtgattaga tgtgcagtta taacttattg aggacatgac cctagataag      3120
aaggtttgga ggatgcgaat taggatagaa ggctagtgca tgtgggaggg ttgtagttag      3180
taattaaggg agcgtcgggg tggggggatat gagggtgggg ggcgcctttg gtttgttagc      3240
gtaggatatt actttatggg tgtcttattt ctgttgttcc atcttgtttc atgtttttat      3300
tatgaatttg tttattactc attgtcttga gccggaggtc tatcggaaac agccttgcta      3360
cttctccgga ggtagtggta tggactgcgt acatcttacc ctccccagac cccactgtgt      3420
gggaatacac tgggtttgtt gttgttattg ttgtaaagat gaaatcgtta tgttgaatga      3480
actccttaat atgggtgtcg cttgctaatt aggtccaatt tcagttcatt cggaaacgcc      3540
cttttgtgat ttgatcataa cagatggaat cttatgttga atgaactcct taatatgagt      3600
gtctcttgct aattaggtcc aaattcagtt cattcagaat cctgaggcgc ccttctgtaa      3660
tatgatcatg aaagatggaa tctttatgtt gaatgaactc ttgaatatga gtttcggttg      3720
ctaattaggt ccaaattccg ttcattcaga agcttgaagt gcccttttat aatttgatca      3780
ttaaagatgg aattttttatg ttcaatgaac tccttaaaat gagtgtcgct tgtaattagg      3840
tccaaattca gttcatccgg aagcttgaac ttctctgttg attctctaca cacacacaca      3900
ctttttaatg tgatgcatgt ttctcttcct gacgagttga ttaaaacatt atattttctt      3960
gaataacata ttaattgctc tcgttctccg aatgtctatt ttttgtgtca atttgctatt      4020
tgttctaatt cttaaatagt attatcttat cttggaaatt tagtgttcca tatttgccaa      4080
agtgacctac agatagttac ttttatacga gttggactaa attctcggcc gattttgtct      4140
acattagcct aagttagagt ttaaacggag tagcatggtc agtgagattt catgtagccg      4200
acccaaactt ctttgaaact gaggagttgt tgtatgctga aatcgtgaat gaaaatgtaa      4260
ctagacaatg gattttggga atagtgtgaa tccttactga ttgctcaggt ttttaacagt      4320
acagatattt ttgttgctta aagcttacga tgaacactca tttttaatat tgagagcaac      4380
tatcatttgc aaattatgct atgcgggcct ttgctgactg tgaacacggt tttgcttatc      4440
acaacacaac ctactggaag ccggttgatt tttgcttgta atatcttgta ggaaggtcct      4500
aagggaagct gcttctggag gaagagatgc tgaacgagtg aaactgaaat tggaaatcaa      4560
agttgaggta aggaaatatt tagacatcca gcatcattca gttgtgaagg ggaagtttaa      4620
cattcttgtt gactgtttaa ttcattttat agtgttagtt ctgaatgcga gtaaaataaa      4680
ttagctgatt gcatctgttc caaagctggg gggaagaata gttttaggcc tactcaatcc      4740
caaaaaccat ctcatggggt gaggattgtc caagaccaca taagagggtc catcccacac      4800
cgatgtgtga cactgacacc accggcgctc ccaagactag acatctgaaa cttagataat      4860
ataacttagg ggcccaacac ttggtaacca agattatgat gggcccaagt ctgaaccatg      4920
tttaaaatgg acctcgggcc taactcaacc cccaatgctc caatagctaa cttatgaggt      4980
gaagcttgcc caagaacaaa ttaggagacc aagcgtccca tctactaccg atgtgggaat      5040
ctaacccccc ctgcatgcac aggccggcaa actgaggtgt ggacaataga caattgggat      5100
```

-continued

```
gcaacatcag gtaaactgag aagtgtgatg attcatgagg tgaggatggc ccaagaggct    5160
aagaccatat aagtacatcc cacaccgatg tgggatacgg accccattct gtagttgtgg    5220
agatagggat ttggtcatgg tacagccaga tagcctttgg tttctcaagt gttggctctg    5280
tgagtacctc atatcgcctt ggggttcaat gaacaatctg aggctattta tatgccattg    5340
ctttgaagat taagcgcttc tgggtgcttg ttgtcgattg tattaggaga ccacaagtat    5400
gactctaatc aatcaagtgg acatttctgg tgttaaggtg ttcctgaagt gacagatgtc    5460
tgctatatga ttacaaatga atagaataga agatgccaag acttggacaa atgtgaactg    5520
caataacttt tagatattga aacggcagat ttgaaggaat catcttctca tggccttttta   5580 tctgcattgt gatcaggtgt gagcctgggt tagaacttga tcttagcttc cagtgtaagg    5640
tgttttaaga gaaattgaaa gataaactta gaaatcaatt aactatagag aaaattttttc   5700 tactaaagca tggagaggag acacttcttt gtcattcttt tccaatgtgg tcgagatgaa    5760
gggtttgggg gttgtttgat gaaatttgag gatatcaata caacctttat atgaaatata    5820
caagatagat ttgcacgtag caatgctcct ttcccaacga atcacattaa atgtgtcatt    5880
tggaaaacaa gaaatagata gtactctttc taggttttca tttgagtgtt ttccatttca    5940
atattgtata atataattaa tttggtgttg tagaatattg agtatgacaa agaaggttct    6000
gccttgcgta ttcgtgggaa gaatatcctg gagaatgaac atgtaaaggt gtgtgttctt    6060
caactaaatc tgtctggata aattctttgc tttgatgctg caaccaaaat ctctaattac    6120
gtttattgca gataggcgct tttcacactc tggaaattga gccacacaga ccttttgtgc    6180
taagaaaggt agaatactgt cttttgattt ggttagcaaa tctatgagca tcttgtttga    6240
ttaaatttta gtcttatctg aacagctttg attttatacg aaagtttaca tataaatcag    6300
ctctgacttg gattatctga tttaggtggt ctgggactca ctggcacgag aggttcttcg    6360
tcaagctgct ggtatgtttc acattgcact ttaacaaaat tatactttta tttgtttaag    6420
tgttgccatt aacattatct gcaatattaa gcgtttagt tcgtaccctt acttttcgtc     6480
catggcttat caagttttac agcctgtaga tacttctttt tagtacatgg atagattaat    6540
aatcaattga cataattgtt aaactgcttt ataggtgcat tagtctcgga tagcttgttt    6600
cagtgtaggt gtgtttttagc ctttattttt gcagaggttc tctactccgc tcaagcactt    6660
gcagtgagaa cataattatt ttctgcaatt tcgtgtgtgt tacagagtgc tgttgaacac    6720
ttgatctgat acgaagtttc tgtacataat tgatgatgtt acagccatat tgattctaac    6780
atggatacgt ggttttgtac tgctcttaga ttaccgtttc attaagctga atccactttt    6840 tcttatttttg atgattcaga tccttctgta agtgctgatc tggctgttgt tctgatgcaa    6900
gaaggattgg cacacatact tcttattggt aaaaggtaag cttgacaatc tgataatcct    6960
ttttgatacg agttttaaac aaattttgag catctccttt tcttttatttt aaacgagatc    7020 aataatttta aaggcgaatg aggatgtccg aatttctatt gcagaattgt atgaaaggtt    7080
aaggctgagt tactagattg tctagcataa ttttgtctta tatacttgtt actgttgtgt    7140
tagcagcttg actattactc gttctcgtat agagacttct ataccacgca agcatggacc    7200
agcaattgca ggttatgata aggtatgtct ccttttgttt cagcttttgt attatttaat    7260
tattttgaag atgaaatctc agtgaaattg agttcttaac tttgatttgc aggcgttaaa    7320
taagttcttt ggcaatgttc tacaggtagt ctctgccagc tttcttgatg tttgcttaat    7380
ctctataagc aatatgttac agactgacag gttcttatttt ctgttgcagg cctttgtcag    7440
```

```
gcatgttgat ttcaaagtag ttcgctgtgc tgtgattgca agtccaggat tcaccaaggt    7500
attttttgtt tttggtttcg ttttgtaaag ttacactctt ggctagtcat tctttaatgc    7560
tatgttacaa cagatagagc atgcatgtct aattatatct gtaccgtaca tatattaatt    7620
cagttgagat attcaattcc ttttgggttg aatatgtagg atcaatttca tcgtcacctg    7680
ttgttagaag ccgagaggaa gcagctaaga cctataatag aaaataaatc acgcatactt    7740
cttgtccata caacctcagg atacaagtaa gcccttttgt aaaaataacc ttcaatattt    7800
gtctatttgt agttgatatg tatgacttat gatgtgcaat gcttgtccag ttcggttgtt    7860
taagcccaat ttttttttct ggttcacaga catagtttga aagaggttct ggatgcccca    7920
aacgtaatga atatgataaa agatacaaaa gctgccaaag aggtacttta cattatgact    7980
cttgctcaac ttaatatgac ctttattcaa tatgcttatg tttgtttatg tcttttttctt    8040 actcttcgag aattacagtt tcttcgtctc ttccaatctt aatcaggttc aagctctaaa    8100 ggaattttttc aacatgcttt caaatgttag gttctatcct tgatctttat gttgtatttg    8160
tatgtttctt aatagctttg ggatatttca gtctctttca tatgctaaga gtacaaccag    8220
attgcttggt tttgaatttt gtttgcttgc tcttttttggt gtttagttcg gctctctgtt    8280
accttgggtt ctgtggaagg cctgagagtt tcaaatgaaa gtctagatgt ttcactatgc    8340
atgacggata ttcctgttta aggagatcaa ggtggactaa tttgaaaatt ttcaacatga    8400
acagacgtag tgttataatg ggcagcgggt gatattgtta tctccgtgtt tgcctttttc    8460
agtcctttct accaattgaa tactgaaaat tcatttgcaa caacaatata cccgcttgtt    8520
acataattta gggatgttat aggtatagag gtcttttgca agagtgattg cctgtttgaa    8580
cgccctccct cagcgtattt catgaattgt gatactaatt ggataaatat gatgccactt    8640
ttcatgcttt cggaagcaac taagaaggat aacacctttt tttaaaagct ttttttccccct    8700 ctttcaagaa ttcctcgcaa taaatgtatg gcgtgtccct tttaccgcat ctcttaacat    8760
atatatgaat gagcttcacc atgtatgaag tttactccca ctagtcaatc taaagatacc    8820
tgtagtgtgt tccttcccgg atacttatgg aagttttttgt tactctattg ggccttctct    8880
aggatcctga tcgtgcatgc tatggaccaa agcatgttga agttgctcac gagcgaatgg    8940
ctatccagac acttctcatt accgacgagc tctttaggtg agtatcttat tttccctggt    9000
tgaacgaatg ggctttacga gcaataaaaa ttaaactgca tatagcttga cagtaatttg    9060
caactctttt ggcatgcttg gcttttaaaa ttgccatcgt tggtgcatag gatttggcaa    9120
tttcattgtt cttcatatgt gaaatcaatt atatattttt cgatttcact catttcctgt    9180
atatagttgg tcgattgttc atgaggaata tctaacttct tttgatctgt tgacaggagt    9240
tctgatgtag aaacgaggaa aaagtatgcc aatctggttg attcagtcaa ggattccggt    9300
ggtactgcac tcatttttctc atcaatgcac gtttcaggag aacgtgagta tatttagtta    9360
cttcctgtta atttccttgt cggaatttat tttagttggc ccctagtaat gctttgaatc    9420
gtatttcctt gtccgttcac atgttcattt tcgcattctc actttacaat cttttttcctt    9480 cctacgagca cacgttgcat atttggttac gctgattata acttatggtt gggaacacag    9540
aactgacaca gctaaccggc attgctgcaa tccttcgttt tcctttgccg gagctggaag    9600
acattgagat gtga                                                       9614
```

<210> SEQ ID NO 8
<211> LENGTH: 3000
<212> TYPE: DNA
<213> ORGANISM: Capsicum annuum

```
<400> SEQUENCE: 8
taaatataac acatagatta attattatta tctttttatc taccatcttt agcacattat         60
tacatattag taaaattaat taggagaaaa agaaaagata tcacaacata tctttattgt        120
cttcacaaat tcttaatttt gtaggttgca tgagtatgac tcttcacttc ttcatgtata        180
tatatatata tatatttcat aaccagttga agaaaaatta ttaacatata ataaatagat        240
aaaataaatt agttagttaa aataaattaa atacacaaaa aaaaaagtat tattcacata        300
aaaattcaaa taatttttcc ttcgtctttc ctgaataaac aatttagata attattaata        360
taatatcaag ttctatgttt aatagttata atatttttat tacacttata ctaaccaaag        420
taactattag aaaaaaagaa gcaatttgat ctatacatga ttctatttat tatttcttga        480
gtgctcacaa gtatagtaat cacatttttt tttctagata attttaacgc aagtaggcca        540
atttagttga gcatgtggta acctcgatca cctgaaaaat tttgaataac atctcacaaa        600
ataaaacaat caacttagac catttctttt aacatgtact ttgacgtgga tatacttttt        660
actattacta tctttactat ctttgataaa aaatgatgca aaattaatac tattcataat        720
ataggtatat aagtatactt aaaaaaatgt gaccaaacac ataaaagatg caaagaaata        780
ttttgaagat aaaatttttc ttacctttat tttgtctttt ttttttcaca ctttggttta        840
ttcacaagtt atatggtgat ggaggagaga aaggataatc ttgaataaaa aatttcatga        900
aataaactat gaatttacac aggcaaaata gggggatatc ataaggtgtc ataaacttat        960
aaattaaatt tgggggttat gaagattaaa atattgaatt tattgatatt attgagagta       1020
taattaaaga tgtgagttat aaataattat ctttattaaa gatatttaat ataaaaagaa       1080
aaaataacta aaataatcac aaaaaaaaga agataaatag taagataata aatggcagcc       1140
cataactctc tattattact gcatcttcat ggaacaactc accttgagtg ttgggctagc       1200
ctcaagcaat gaatattaag tgaccctctg tttctaaaat aaaatttgga caaatatata       1260
tctctaacta aaaaaggata caattttgct tgaatttgaa agtttaataa gtgaaacttt       1320
agtatgattt cggattgcaa cgtttaggaa caaattcaaa agtttaaatt tttattaatt       1380
caaatttcag aaaaattcat gaaattcaat attttttgttg attcaaacac caaaacaatt       1440
catgaaattt gatgtttta aaaaataatg ccactgtgag agttgactta agaagcaacc       1500
tgccataaaa cttagtcgac agcctcagct agccatttat aacaaatcaa tgtaaacttt       1560
ttaaacatca aaatccaaaa aatttcgtgg agtttaaaat aactatcaca aacgaaatat       1620 attctttag ttataatatc tcttttgaat ttaattatat ctccttcggg tttcaacttg       1680
taatgccagc taaaatttaa ttagcaattc taaaagggac tatatatcta ttactttcca       1740
tattttagat gtgtaagtta cgtatttact ttcaaaatgt gattacttgt gttttttcaag       1800 cttaaataca caaactaatt agaatcatat gaatagaatt aaacagtgag cattacgtat       1860
acatgtataa caatatctgg taagaaaata cgaaattgaa catccaaagt cagaagcata       1920
aaacaaactc ttcatttagc agccccatcc tatctaatga ctaatatcaa aataacaata       1980
aaccccaaaa agacggggga acggaaagta agaaaacaaa agtggctcca aaagatagag       2040
acatgattta caagaaaaac tacacatcta taatactatg aacctatagg gcatactatt       2100
attaggctaa taaggtaaat gtatacaaga atcgttgaaa gttacttgat gaaagcagca       2160
actggaacaa caactttgct aagcataatt tgatatggtg atgaagaaga gaaaggataa       2220
tcttgaatga aattttcatg aaacaaacta taaatttata taggcaaaat gaaggaatac       2280
```

-continued

```
cataaggtgt cataaactta taaattaaat tttggggtta tgaagattaa aaggttgaat      2340
ttattgatat tattaagagt ataattgaag gtatgagtta taaataatta tatttattaa      2400
agacattaaa tataaaaaga agaaaaatat tcaaatataa ggaaaaaaat gacccagaaa      2460
accacaaaat agataaatag tattggaggc ctctaagaca tgccacatag gattgtctta      2520
gagtttcctt tatatatata ttgattgtaa gatttttttt tttgaatttt gtaataaaaa      2580
taaataaatt aaatgaatat tgagaattaa catgatgatt attaaagttt taaaatttta      2640
aaaggacaaa aataaaaaaa tatgactaat ttatatatat tttttaatat gtgtgtcaaa      2700
ttctaataat ttaattattt taaaatggaa gaagtatatt ttattttatt tttctaatat      2760
aacactacat cgcgatcctt ttccaattag attctatatg ctatttttat tcttacggtg      2820
cttacgttat tttttcatta tttttccaat tgtttagtat ttgaccttaa tatacgatag      2880
tcttggaaaa aaacaaaaaa aactacacat acaagaacac tccaacctttt aaacctgcaa      2940 cttcccatca aactgaagca aatctcttac aaaaaaagaa ccaattttta ataattaaat      3000
```

<210> SEQ ID NO 9
<211> LENGTH: 21
<212> TYPE: DNA
<213> ORGANISM: artificial sequence
<220> FEATURE:
<223> OTHER INFORMATION: primer used to detect BCTV

<400> SEQUENCE: 9

```
ctacacgaag atgggcaacc t                                                  21
```

<210> SEQ ID NO 10
<211> LENGTH: 21
<212> TYPE: DNA
<213> ORGANISM: artificial sequence
<220> FEATURE:
<223> OTHER INFORMATION: primer used to detect BCTV

<400> SEQUENCE: 10

```
tgacgtcgga gctggatttta g                                                 21
```

<210> SEQ ID NO 11
<211> LENGTH: 358
<212> TYPE: PRT
<213> ORGANISM: Cucurbita pepo

<400> SEQUENCE: 11

```
Met Lys Ile Val Arg Lys Gln Leu Asp Gln Asn Gly Ser Gly Ser Val
1               5                   10                  15

Lys Met Val Pro Leu Asp Ser Asp Asp Leu Trp His Ala Phe Asn Leu
            20                  25                  30

Ile Ala Pro Gly Asp Thr Val Met Ala Val Thr Val Arg Lys Val Ile
        35                  40                  45

Arg Glu Met Ala Ser Gly Gly Arg Asp Ala Glu Arg Val Lys Leu Lys
    50                  55                  60

Leu Glu Ile Lys Val Glu Glu Ile Gly Ala Tyr His Thr Leu Glu Leu
65                  70                  75                  80

Glu Leu His Arg Pro Phe Val Leu Arg Lys Asp Val Trp Asp Ser Phe
                85                  90                  95

Ala Leu Asp Val Leu His Gln Ala Ser Gly Met Phe Leu Asp Pro Ala
            100                 105                 110

Ala Ser Ala Asp Leu Ala Val Val Leu Met Gln Glu Gly Leu Ala His
            115                 120                 125
```

```
Val Ile Leu Val Gly Lys Ser Met Thr Ile Thr Arg Ala Arg Ile Glu
    130             135             140

Thr Ser Ile Pro Arg Lys His Gly Ser Ala Ile Ala Gly Tyr Glu Ser
145             150             155             160

Ala Leu Asn Lys Phe Phe Glu Asn Val Leu Gln Ala Phe Leu Lys His
            165             170             175

Val Asp Phe Lys Val Val Arg Cys Ala Val Ile Ala Ser Pro Gly Phe
            180             185             190

Thr Lys Asp Gln Phe His Arg His Leu Leu Leu Glu Ala Glu Arg Arg
            195             200             205

Gln Leu Arg Pro Ile Ile Glu Asn Lys Ser Arg Ile Ile Leu Thr His
    210             215             220

Thr Thr Ser Gly Tyr Lys His Ser Leu Arg Glu Val Leu Asp Ala Ser
225             230             235             240

Asn Val Met Asn Met Ile Lys Asp Thr Lys Ala Ala Gln Glu Val Arg
            245             250             255

Ala Leu Lys Asp Phe Phe Thr Met Leu Ser Asn Glu Pro Asp Arg Ala
            260             265             270

Cys Tyr Gly Pro Lys His Val Glu Val Ala His Glu Arg Met Ala Ile
            275             280             285

Gln Thr Leu Leu Ile Thr Asp Asp Leu Phe Arg Asn Asn Asp Ile Thr
    290             295             300

Glu Arg Gln Lys Tyr Val Asn Leu Val Asp Ser Val Lys Asp Ser Gly
305             310             315             320

Gly Thr Val His Ile Phe Ser Ser Met His Val Ser Gly Glu Gln Leu
            325             330             335

Ala Gln Ile Thr Gly Ile Ala Ala Ile Leu Arg Phe Pro Leu Pro Glu
            340             345             350

Leu Glu Asp Ile Glu Met
            355

<210> SEQ ID NO 12
<211> LENGTH: 378
<212> TYPE: PRT
<213> ORGANISM: Manihot esculenta

<400> SEQUENCE: 12

Met Lys Ile Thr Arg Arg Asn Leu Val Pro Asp Gly Pro Gly Ser Val
1               5               10              15

Lys Met Thr Pro Val Asp Ser Asp Asp Leu Trp Phe Val Tyr Asn Leu
            20              25              30

Ile Ser Pro Gly Asp Ser Val Met Ala Asp Thr Val Arg Lys Val Leu
            35              40              45

Arg Glu Ala Ala Ser Gly Gly Arg Asp Ala Glu Arg Val Arg Leu Lys
    50              55              60

Leu Glu Ile Lys Val Glu Thr Val Asp Tyr Asp Lys Val Gly Ala Ala
65              70              75              80

Leu Arg Ile Arg Gly Lys Asn Ile Leu Glu Asn Glu Tyr Val Lys Ile
            85              90              95

Gly Ala Phe His Thr Leu Glu Leu Glu Leu Gln Arg Pro Phe Val Leu
            100             105             110

Arg Lys Glu Val Trp Asp Ser Met Ala Leu Asp Val Leu Asn Gln Ala
            115             120             125

Ser Asp Pro Gly Ala Ser Ala Asp Leu Ala Val Val Leu Met Gln Glu
```

-continued

```
              130              135              140
Gly Leu Ala His Ile Leu Leu Val Gly Lys Ser Val Thr Thr Thr Arg
145              150              155              160

Ser Arg Ile Glu Thr Ser Ile Pro Arg Lys His Gly Pro Ala Ile Ala
                 165              170              175

Gly Tyr Glu Ser Ala Leu Asn Lys Phe Phe Glu His Val Leu Gln Ala
                 180              185              190

Phe Leu Lys His Ile Asp Phe Ser Val Ile Arg Cys Ala Val Ile Ala
                 195              200              205

Ser Pro Gly Phe Thr Lys Asp Gln Phe His Arg His Leu Leu Leu Glu
    210              215              220

Ala Glu Arg Arg Gln Leu Arg Pro Ile Ile Glu Asn Lys Ser Arg Ile
225              230              235              240

Val Leu Val His Thr Ser Ser Gly Tyr Lys His Ser Leu Arg Glu Val
                 245              250              255

Leu Asp Ala Pro Asn Val Met Asn Met Ile Lys Asp Thr Lys Ala Ala
                 260              265              270

Gln Glu Val Arg Ala Leu Glu Asp Phe Phe Asn Met Leu Ser Asn Asp
                 275              280              285

Pro Ala Arg Ala Cys Tyr Gly Pro Lys His Val Glu Val Ala His Glu
    290              295              300

Arg Met Ala Val Gln Thr Leu Leu Ile Thr Asp Asp Leu Phe Arg Asn
305              310              315              320

Ala Asp Ile Pro Thr Arg Gln Lys Tyr Ile Asn Leu Val Asn Ser Val
                 325              330              335

Lys Gly Ser Gly Gly Thr Ala His Ile Phe Ser Ser Met His Val Ser
                 340              345              350

Gly Glu Gln Leu Ala Gln Leu Thr Gly Ile Ala Ala Ile Leu Arg Phe
                 355              360              365

Pro Leu Pro Asp Leu Glu Asp Ile Glu Met
    370              375

<210> SEQ ID NO 13
<211> LENGTH: 377
<212> TYPE: PRT
<213> ORGANISM: Gossypium hirsutum

<400> SEQUENCE: 13

Met Lys Val Val His Arg Asp Leu Val Pro Asn Gly Pro Gly Ser Val
1               5               10              15

Lys Met Ile Pro Val Asp Ser Glu Asp Leu Trp Phe Ala Tyr Asn Leu
                 20              25              30

Ile Ala Thr Gly Asp Trp Val Met Ser Arg Thr Val Arg Lys Val Leu
                 35              40              45

Arg Glu Thr Ala Gly Gly Arg Asp Ala Glu Arg Val Ala Leu Lys Leu
    50              55              60

Glu Ile Lys Val Glu Ala Ile Asp Tyr Asp Lys Glu Gly Ser Val Leu
65              70              75              80

Arg Ile Arg Gly Lys Asn Thr Leu Glu Asn Glu His Val Lys Ile Gly
                 85              90              95

Gln Phe His Thr Leu Glu Leu Glu Leu Gln Arg Pro Phe Val Leu Arg
                 100             105             110

Lys Lys Ile Trp Asp Ser Leu Ala Leu Asp Val Leu Arg Gln Ala Ser
                 115             120             125
```

-continued

```
Asp Pro Gly Ala Ser Ala Asp Leu Ala Val Val Leu Met Gln Glu Gly
    130                 135                 140

Leu Ala Asn Ile Leu Leu Val Gly Lys Ser Met Thr Ser Thr Arg Ser
145                 150                 155                 160

Arg Ile Glu Thr Ser Ile Pro Arg Lys His Gly Pro Ala Ile Ala Gly
                165                 170                 175

Tyr Glu Ser Ala Leu Lys Lys Phe Phe Glu Asn Val Leu Gln Ala Phe
                180                 185                 190

Leu Lys His Val Asp Phe Asn Val Val Arg Cys Ala Val Ile Ala Ser
            195                 200                 205

Pro Gly Phe Thr Lys Glu Gln Phe His Arg His Leu Met Leu Glu Ala
    210                 215                 220

Glu Arg Arg Gln Leu Arg Pro Ile Ile Glu Asn Lys Ser Arg Ile Ile
225                 230                 235                 240

Leu Val His Thr Ser Ser Gly Tyr Lys His Ser Leu Arg Glu Val Leu
                245                 250                 255

Asp Ala Pro Asn Val Met Ser Met Ile Lys Asp Thr Lys Ala Ala Gln
                260                 265                 270

Glu Val Arg Ala Leu Lys Asp Phe Phe Asn Met Leu Ser Asn Asp Pro
            275                 280                 285

Ala Arg Ala Cys Tyr Gly Pro Lys His Val Glu Ile Ala His Glu Arg
    290                 295                 300

Met Ala Val Gln Thr Leu Leu Ile Thr Asp Asp Leu Phe Arg Asn Ser
305                 310                 315                 320

Asp Val Ile Thr Arg Gln Lys Tyr Val Ser Leu Val Asn Ser Val Lys
                325                 330                 335

Asn Ser Gly Gly Thr Ala His Ile Phe Ser Ser Met His Val Ser Gly
                340                 345                 350

Glu Gln Leu Ala Gln Leu Thr Gly Ile Ala Ala Ile Leu Arg Phe Pro
            355                 360                 365

Leu Pro Asp Leu Glu Asp Ile Glu Met
    370                 375

<210> SEQ ID NO 14
<211> LENGTH: 377
<212> TYPE: PRT
<213> ORGANISM: Gossypium hirsutum

<400> SEQUENCE: 14

Met Lys Val Val His Arg Asp Leu Val Pro Asn Gly Pro Gly Ser Val
1               5                   10                  15

Lys Met Ile Pro Val Asp Ser Glu Asp Leu Trp Phe Ala Tyr Asn Leu
                20                  25                  30

Ile Ala Thr Gly Asp Trp Val Met Ala Arg Thr Val Arg Lys Val Leu
                35                  40                  45

Arg Glu Thr Ala Gly Gly Arg Asp Ala Glu Arg Val Ala Leu Lys Leu
    50                  55                  60

Glu Ile Lys Val Glu Ala Ile Asp Tyr Asp Lys Glu Gly Ser Val Leu
65                  70                  75                  80

Arg Ile Arg Gly Lys Asn Thr Leu Glu Asn Glu His Val Lys Ile Gly
                85                  90                  95

Gln Phe His Thr Leu Glu Leu Glu Leu Gln Arg Pro Phe Val Leu Arg
                100                 105                 110

Lys Lys Ile Trp Asp Ser Leu Ala Leu His Val Leu Arg Gln Ala Ser
            115                 120                 125
```

```
Asp Pro Gly Ala Ser Ala Asp Leu Ala Val Val Leu Met Gln Glu Gly
    130                 135                 140

Leu Ala Asn Ile Leu Leu Val Gly Lys Ser Met Thr Ser Thr Arg Ser
145                 150                 155                 160

Arg Ile Glu Thr Ser Ile Pro Arg Lys His Gly Pro Ala Ile Ala Gly
                165                 170                 175

Tyr Glu Ser Ala Leu Lys Lys Phe Phe Glu Asn Val Leu Gln Ala Phe
                180                 185                 190

Leu Lys His Val Asp Phe Asn Val Val Arg Cys Ala Val Ile Ala Ser
                195                 200                 205

Pro Gly Phe Thr Lys Asp Gln Phe His Arg His Leu Met Leu Glu Ala
    210                 215                 220

Glu Arg Arg Gln Leu Arg Pro Ile Ile Glu Asn Lys Ser Arg Ile Ile
225                 230                 235                 240

Leu Val His Thr Ser Ser Gly Tyr Lys His Ser Leu Lys Glu Val Leu
                245                 250                 255

Asp Ala Pro Asn Val Met Ser Met Ile Lys Asp Thr Lys Ala Ala Gln
                260                 265                 270

Glu Val Arg Ala Leu Lys Asp Phe Phe Asn Met Leu Ser Asn Asp Pro
                275                 280                 285

Ala Arg Ala Cys Tyr Gly Pro Lys His Val Glu Val Ala His Glu Arg
    290                 295                 300

Met Ala Val Gln Thr Leu Leu Ile Thr Asp Asp Leu Phe Arg Asn Ser
305                 310                 315                 320

Asp Val Ile Thr Arg Gln Lys Tyr Val Gly Leu Val Asn Ser Val Lys
                325                 330                 335

Asn Ser Gly Gly Thr Ala His Ile Phe Ser Ser Met His Val Ser Gly
                340                 345                 350

Glu Gln Leu Ala Gln Leu Thr Gly Ile Ala Ala Ile Leu Arg Phe Pro
                355                 360                 365

Leu Pro Asp Leu Glu Asp Ile Glu Met
    370                 375
```

<210> SEQ ID NO 15
<211> LENGTH: 379
<212> TYPE: PRT
<213> ORGANISM: Glycine max

<400> SEQUENCE: 15

```
Met Lys Ile Val Arg Lys Asp Leu Val Pro Asn Gly Pro Gly Ser Val
1                 5                   10                  15

Lys Met Val Ala Val Asp Ser Asp Asp Leu Trp Phe Ala Tyr Asn Leu
                20                  25                  30

Ile Ala Pro Gly Asp Ser Val Met Ala Val Thr Val Arg Lys Val Leu
                35                  40                  45

Arg Glu Ala Ala Ser Gly Gly Arg Glu Ala Glu Arg Val Lys Leu Lys
    50                  55                  60

Leu Glu Ile Lys Val Gln Glu Leu Ala Asp Tyr Asp Lys Glu Gly Ser
65                  70                  75                  80

Ile Leu Arg Val Arg Gly Lys Asn Ile Leu Glu Asn Glu Tyr Val Lys
                85                  90                  95

Ile Gly Ala Phe His Thr Leu Glu Leu Glu Leu Gln Arg Pro Phe Val
                100                 105                 110

Leu Arg Lys Asp Val Trp Asp Ser Leu Ala Leu Glu Val Leu Gln Gln
```

-continued

```
                    115                 120                 125

Ala Ser Asp Pro Gly Ala Ser Ala Asp Leu Ala Val Val Leu Met Gln
        130                 135                 140

Glu Gly Leu Ala His Ile Leu Leu Val Gly Arg Ser Met Thr Val Thr
145                 150                 155                 160

Arg Ser Arg Ile Glu Thr Ser Ile Pro Arg Lys His Gly Pro Ala Ile
                    165                 170                 175

Ala Gly Tyr Glu Lys Ala Leu Asp Lys Phe Phe Gln Asn Val Leu Gln
                180                 185                 190

Ala Phe Leu Lys His Ile Asp Phe Asn Val Val Arg Cys Ala Val Ile
            195                 200                 205

Ala Ser Pro Gly Phe Thr Lys Asp Gln Phe His Arg His Leu Phe Leu
        210                 215                 220

Glu Ala Glu Arg Arg Gln Leu Arg Pro Ile Ile Glu Asn Lys Ser Arg
225                 230                 235                 240

Ile Ile Leu Val His Thr Ser Ser Gly Tyr Lys His Ser Leu Lys Glu
                    245                 250                 255

Val Leu Asp Ala Pro Asn Val Met Ser Leu Ile Lys Asp Thr Lys Ala
                260                 265                 270

Ala Gln Glu Val Arg Val Met Lys Asp Phe Tyr Asp Met Leu Ser Asn
            275                 280                 285

Asp Pro Ser Arg Ala Cys Tyr Gly Met Lys His Val Glu Val Ala Asn
        290                 295                 300

Glu Arg Leu Ala Val Gln Thr Leu Leu Ile Thr Asp Glu Leu Phe Arg
305                 310                 315                 320

Asn Ser Asp Ile Ala Thr Arg Lys Lys Tyr Val Asn Leu Val Asn Ser
                    325                 330                 335

Val Lys Asp Ser Gly Gly Ser Val His Val Phe Ser Ser Met His Val
                340                 345                 350

Ser Gly Glu Gln Leu Ala Gln Ile Ser Gly Ile Ala Ala Ile Leu Arg
            355                 360                 365

Phe Pro Leu Pro Asp Leu Glu Asp Ile Glu Met
        370                 375

<210> SEQ ID NO 16
<211> LENGTH: 379
<212> TYPE: PRT
<213> ORGANISM: Glycine max

<400> SEQUENCE: 16

Met Lys Ile Val Arg Arg Asp Leu Val Pro Asn Gly Pro Gly Ser Val
1                   5                   10                  15

Lys Met Val Ala Val Asp Ser Asp Asp Leu Trp Phe Ala Tyr Asn Leu
            20                  25                  30

Ile Ala Pro Gly Asp Ser Val Met Ala Val Thr Val Arg Lys Val Leu
        35                  40                  45

Arg Glu Ala Ala Asn Gly Gly Arg Glu Ala Glu Arg Val Lys Leu Lys
        50                  55                  60

Leu Glu Ile Lys Val Glu Glu Leu Ser Asp Tyr Asp Lys Glu Gly Ser
65                  70                  75                  80

Ile Leu Arg Val Arg Gly Lys Asn Ile Leu Glu Asn Glu Tyr Val Lys
                    85                  90                  95

Ile Gly Ala Phe His Thr Leu Glu Leu Glu Leu Gln Arg Pro Phe Val
                100                 105                 110
```

```
Leu Arg Lys Asp Val Trp Asp Ser Leu Ala Leu Glu Val Leu Gln Gln
        115                 120                 125

Ala Ser Asp Pro Gly Ala Ser Ala Asp Leu Ala Val Val Leu Met Gln
        130                 135                 140

Glu Gly Leu Ala His Ile Leu Leu Val Gly Arg Ser Met Thr Val Thr
145                 150                 155                 160

Arg Ser Arg Ile Glu Thr Ser Ile Pro Arg Lys His Gly Pro Ala Ile
                165                 170                 175

Ala Gly Tyr Glu Lys Ala Leu Asp Lys Phe Phe Gln Asn Val Leu Gln
                180                 185                 190

Ala Phe Leu Lys His Ile Asp Phe Asn Val Val Arg Cys Ala Val Ile
                195                 200                 205

Ala Ser Pro Gly Phe Thr Lys Asp Gln Phe His Arg His Leu Phe Leu
        210                 215                 220

Glu Ala Glu Arg Arg Gln Leu Arg Pro Ile Ile Glu Asn Lys Ser Arg
225                 230                 235                 240

Ile Ile Leu Val His Thr Ser Ser Gly Tyr Lys His Ser Leu Lys Glu
                245                 250                 255

Val Leu Asp Ala Pro Asn Val Met Ser Leu Ile Lys Asp Thr Lys Ala
                260                 265                 270

Ala Gln Glu Val Arg Val Met Lys Asp Phe Tyr Asp Met Leu Ser Asn
        275                 280                 285

Asp Pro Ser Arg Ala Cys Tyr Gly Met Lys His Val Glu Val Ala Asn
        290                 295                 300

Glu Arg Leu Ala Val Gln Met Leu Leu Ile Thr Asp Glu Leu Phe Arg
305                 310                 315                 320

Asn Ser Asp Ile Ala Thr Arg Lys Lys Tyr Val Asn Leu Val Asn Ser
                325                 330                 335

Val Lys Asp Ser Gly Gly Ser Val His Val Phe Ser Ser Met His Val
                340                 345                 350

Ser Gly Glu Gln Leu Ala Gln Ile Ser Gly Ile Ala Ala Ile Leu Arg
        355                 360                 365

Phe Pro Leu Pro Asp Leu Glu Asp Ile Glu Met
    370                 375

<210> SEQ ID NO 17
<211> LENGTH: 378
<212> TYPE: PRT
<213> ORGANISM: Arabidopsis thaliana

<400> SEQUENCE: 17

Met Lys Ile Val Arg Arg Asp Phe Val Arg Asn Gly Pro Gly Ser Val
1                   5                   10                  15

Lys Met Val Ala Glu Asp Ser Asp Asp Leu Trp Tyr Ala Tyr Asn Leu
            20                  25                  30

Ile Ala Val Gly Asp Ser Val Met Ala Val Thr Phe Arg Lys Val Gln
        35                  40                  45

Arg Glu Ile Pro Gly Gly Arg Asp Ser Glu Arg Val Lys Leu Lys
    50                  55                  60

Leu Glu Val Gln Val Glu Glu Val Asp Tyr Asp Lys Asp Gly Ser Val
65                  70                  75                  80

Leu Arg Ile Arg Gly Lys Asn Ile Leu Glu Asn Glu His Val Lys Ile
                85                  90                  95

Gly Ala Phe His Thr Leu Glu Leu Glu Leu Lys Arg Pro Phe Val Leu
            100                 105                 110
```

```
Arg Lys Glu Met Trp Asp Ser Met Ala Leu Asp Thr Leu Lys Gln Ala
        115                 120                 125

Ser Asp Pro Ala Ala Ser Ala Asp Leu Ala Val Val Leu Met Gln Glu
        130                 135                 140

Gly Leu Ala Gln Ile Phe Leu Val Gly Arg Ser Val Thr Ser Ser Arg
145                 150                 155                 160

Ala Arg Ile Glu Thr Ser Ile Pro Arg Lys His Gly Pro Ala Ile Ala
                165                 170                 175

Gly Tyr Glu Ser Ala Leu Lys Lys Phe Phe Glu Asn Val Leu Gln Ala
                180                 185                 190

Phe Val Lys His Val Asp Phe Ser Val Val Arg Cys Ala Val Val Ala
        195                 200                 205

Ser Pro Gly Phe Thr Lys Asp Gln Phe His Arg His Leu Leu Leu Glu
        210                 215                 220

Ala Glu Arg Arg Gln Leu Arg Pro Ile Ile Glu Asn Lys Ser Arg Ile
225                 230                 235                 240

Ile Leu Val His Thr Asn Ser Gly Tyr Arg His Ser Leu Gly Glu Val
                245                 250                 255

Leu His Ala Pro Asn Val Met Asn Met Ile Lys Asp Thr Lys Ala Ala
                260                 265                 270

Lys Glu Val Lys Ala Leu Asn Asp Phe His Asn Met Leu Ser Thr Glu
        275                 280                 285

Pro Asp Arg Ala Cys Tyr Gly Pro Lys His Val Glu Val Ala Asn Glu
        290                 295                 300

Arg Met Ala Ile Gln Thr Leu Leu Ile Thr Asp Glu Leu Phe Arg Asn
305                 310                 315                 320

Ser Asp Val Lys Thr Arg Lys Lys Tyr Val Asn Leu Val Glu Ser Val
                325                 330                 335

Lys Asp Ser Gly Gly Asp Ala Phe Ile Phe Ser Ala Met His Val Ser
                340                 345                 350

Gly Glu Gln Leu Ala Gln Leu Thr Gly Ile Ala Ala Leu Leu Arg Phe
        355                 360                 365

Pro Leu Pro Glu Leu Glu Asp Ile Glu Met
        370                 375

<210> SEQ ID NO 18
<211> LENGTH: 378
<212> TYPE: PRT
<213> ORGANISM: solanum lycopersicum

<400> SEQUENCE: 18

Met Lys Ile Val Arg Arg Asp Phe Val Pro Asp Gly Ser Gly Ser Gly
1               5                   10                  15

Lys Ile Ile Pro Glu Glu Ala Asp Asp Leu Trp Val Ala Tyr Asn Leu
                20                  25                  30

Ile Ala Glu Gly Asp Thr Val Leu Ala Val Thr Val Arg Lys Val Leu
        35                  40                  45

Arg Glu Ala Ala Ser Gly Gly Arg Asp Ala Glu Arg Val Lys Leu Lys
        50                  55                  60

Leu Glu Ile Lys Val Glu Asn Val Glu Tyr Asp Lys Glu Gly Ser Ala
65                  70                  75                  80

Leu Arg Ile Arg Gly Lys Asn Ile Leu Glu Asn Glu His Val Lys Ile
                85                  90                  95

Gly Ala Phe His Thr Leu Glu Ile Glu Gln His Arg Pro Phe Val Leu
```

-continued

```
                    100              105              110

Arg Lys Val Val Trp Asp Ser Leu Ala Arg Glu Val Leu Arg Gln Ala
        115              120              125

Ser Asp Pro Ser Ala Ser Ala Asp Leu Ala Val Val Leu Met Gln Glu
    130              135              140

Gly Leu Ala His Ile Leu Leu Ile Gly Lys Ser Val Thr Ile Thr Arg
145              150              155              160

Ser Arg Ile Glu Ser Ser Ile Pro Arg Lys His Gly Pro Ala Ile Ala
                165              170              175

Gly Tyr Asp Lys Ala Leu Asn Lys Phe Phe Asp Asn Val Leu Gln Ala
            180              185              190

Phe Val Lys His Val Asp Phe Lys Val Val Arg Cys Ala Val Ile Ala
            195              200              205

Ser Pro Gly Phe Thr Lys Asp Gln Phe His Arg His Leu Leu Leu Glu
    210              215              220

Ala Glu Arg Lys Gln Leu Arg Pro Ile Ile Glu Asn Lys Ser Arg Ile
225              230              235              240

Ile Leu Val His Thr Thr Ser Gly Tyr Lys His Ser Leu Lys Glu Val
                245              250              255

Met Asp Ala Pro Asn Val Met Thr Met Ile Lys Asp Thr Lys Ala Ala
            260              265              270

Lys Glu Val Gln Ala Leu Lys Asp Phe Phe Asn Met Leu Ser Asn Asp
    275              280              285

Pro Asp Arg Ala Cys Tyr Gly Pro Lys His Val Glu Val Ala His Glu
    290              295              300

Arg Leu Ala Ile Gln Thr Leu Leu Ile Thr Asp Glu Leu Phe Arg Ser
305              310              315              320

Ser Asp Val Glu Thr Arg Lys Lys Tyr Ala Asn Leu Val Asp Ser Val
                325              330              335

Lys Asp Ser Gly Gly Thr Ala Leu Ile Phe Ser Ser Met His Val Ser
            340              345              350

Gly Glu Gln Leu Asn Gln Leu Thr Gly Ile Ala Ala Ile Leu Arg Phe
            355              360              365

Pro Leu Pro Glu Leu Glu Asp Ile Glu Met
    370              375

<210> SEQ ID NO 19
<211> LENGTH: 1077
<212> TYPE: DNA
<213> ORGANISM: Cucurbita pepo

<400> SEQUENCE: 19
atgaagatcg tacgcaaaca gcttgatcag aatgggtctg gtagtgtcaa gatggtgcca      60
cttgattcag atgatctatg gcatgcgttc aatttgattg ctccgggaga cactgttatg     120
gctgtcaccg ttaggaaagt catcagagag atggcttctg gaggaagaga tgcagaacga     180
gtgaaactca agctagaaat aaaagttgag gagataggg cttaccatac tttagaactt     240
gagctgcatc ggccatttgt tttgagaaag gatgtttggg actctttgc tctagatgta     300 cttcatcaag cctctggtat gtttctggat cctgctgcta gtgctgactt ggccgtggtt     360
ttaatgcaag aaggattagc acatgttatt cttgtcggaa aaagtatgac aattactcga     420
gctcgaatcg aaacttcaat tcctcgcaag catgggtcag ccattgctgg ttatgagtcg     480
gccttgaata aattcttcga gaatgtttta caggctttct tgaagcatgt tgattttaaa     540
```

-continued

```
gtggtacgct gtgcagtgat agctagtcct ggatttacca aggatcagtt ccatcggcac    600
ttattattgg aagctgaaag aagacagcta agacctatta tcgagaacaa atcccgcata    660
attctaacac atacaacctc aggatacaag catagtttac gagaggtttt ggatgcttca    720
aatgtcatga atatgataaa agacactaaa gcagctcaag aggtgcgagc tctaaaggat    780
ttctttacca tgctctctaa tgagccagac cgtgcttgtt atggaccaaa acacgtggag    840
gttgcccatg aacgaatggc tattcaaacg cttctcatta ctgatgatct cttcaggaat    900
aatgatataa cggagcgaca aaaatacgtc aatttggtcg attcagttaa ggattcaggt    960
ggcaccgttc atatattttc atccatgcac gtctctggag agcaactcgc tcagataact   1020
ggaattgcag caatccttcg atttcctctg ccggaactcg aggacataga gatgtaa      1077
```

<210> SEQ ID NO 20
<211> LENGTH: 1137
<212> TYPE: DNA
<213> ORGANISM: Manihot esculenta

<400> SEQUENCE: 20

```
atgaagatca cacgaagaaa cctcgtgccg gacggccccg gtagtgtcaa gatgacgcca     60
gtcgattcag atgatctttg gttcgtttat aatttgatat ctccgggtga ttcggttatg    120
gcggatactg tcaggaaagt tttgagagag gcggcgtccg gtgggagaga tgctgaaaga    180
gtgaggctga agttggaaat aaaagttgag actgtagatt atgataaagt tggggctgcc    240
ttgcgaattc gcggaaagaa tattttggag aatgaatatg taaagattgg agcatttcac    300
actttagagt tagagctgca acgccctttt gttttgagaa aggaagtttg ggactcaatg    360
gcattagatg tactcaatca agcctctgat cccggtgcaa gtgctgatct tgctgtggtt    420
ttaatgcaag aaggacttgc acacatctta cttgtcggta aaagcgtgac aactactcga    480
tcaaggatag agacttcaat tcctcgaaag catggccctg ccattgctgg ttatgaatcg    540
gcattgaata agttctttga gcatgtttta caggctttcc taaagcatat tgatttcagt    600
gtcattcggt gtgcggtgat tgcaagccct ggtttcacta aggatcagtt tcatcgtcac    660
ttattgttgg aggcagagag gagacagctg agacccatta ttgagaacaa gtcacgcata    720
gtgctcgtgc atacaagctc aggatataag catagcttga gggaggttct tgatgcccca    780
aatgttatga acatgattaa agacactaag gcagcacaag aggttcgagc actcgaggat    840
ttctttaaca tgctttcaaa tgatccagct cgtgcatgct atggaccaaa gcatgtagag    900
gttgcccatg aacgcatggc tgtccaaact cttctcatca cagatgatct tttcagaaat    960
gccgatatac caacgaggca gaagtacatc aatctagtca actcagtgaa gggttcaggg   1020
ggcactgctc atatattttc atcaatgcat gtctcagggg agcaattggc gcaattgacc   1080
ggcattgctg ccatacttcg atttccgctg ccagacctgg aagacattga gatgtaa      1137
```

<210> SEQ ID NO 21
<211> LENGTH: 1134
<212> TYPE: DNA
<213> ORGANISM: Gossypium hirsutum

<400> SEQUENCE: 21

```
atgaaggtcg tacaccgaga cctagttccc aatggccctg gcagcgtcaa gatgatacca     60
gtggattcag aggatctctg gtttgcttac aatttgatag ctactgggga ttgggttatg    120
tctcgaaccg tcaggaaagt tctaagggag acagccggtg aagagatgc agagcgtgtt    180 gccctgaagt tggaaataaa agtcgaggcc atagattatg acaaagaagg atctgtcttg    240
```

-continued

```
cgtataaggg gaaagaacac cttggagaat gagcatgtta agataggaca attccatact      300
ctcgaacttg agcttcagcg accttttgtt ttaagaaaga aaatatggga ctcattggca      360
ttagatgttc tccgacaggc ctctgatcct ggtgcgagtg cagatctggc tgtggtacta      420
atgcaagaag ggctagcaaa tattttactt gttggtaaaa gtatgacaag tacccgttca      480
cggattgaaa cttcaattcc tcgtaagcat ggacctgcca ttgctggtta tgaatcggct      540
ttgaagaagt tctttgagaa tgttctacag gctttcctca aacatgtgga tttcaatgtt      600
gttcgctgtg ctgttattgc tagtcctggc ttcacaaagg aacagttcca tcgtcatctt      660
atgttggagg cagaaagaag acaattgagg ccaattattg agaataagtc gcgaataatt      720
cttgttcata caagctccgg atataagcat agtttgagag aagtcttgga tgccccaaat      780
gttatgagca tgataaaaga caccaaagca gcgcaagagg tccgagcact caaggatttc      840
ttcaacatgc tttcaaatga tccggcacgt gcatgctacg gaccaaaaca tgtggagatt      900
gcccatgagc gaatggcagt tcaaacactt cttattaccg acgatctctt caggaattcg      960
gacgtaatta cgaggcaaaa gtatgtcagt ttggtgaact ccgttaagaa ttcggggggc     1020
actgctcaca tttttttcgtc tatgcacgta tcaggggaac aactggcaca gctgaccggc     1080
attgcggcaa tccttcgttt ccctcttccg gatctggaag acatcgaaat gtag           1134
```

```
<210> SEQ ID NO 22
<211> LENGTH: 1134
<212> TYPE: DNA
<213> ORGANISM: Gossypium hirsutum

<400> SEQUENCE: 22
```

```
atgaaggtcg tacaccgaga cctagttccc aatggccctg gcagcgtcaa gatgatacca       60
gtggattcag aggatctctg gtttgcttac aatttgatag ctactgggga ttgggttatg      120
gctcgaactg tcaggaaagt tctaagggag acagccggtg aaagagatgc agagcgtgtt      180
gccctgaagt tggaaataaa agtcgaggcc atagattatg acaaagaagg atctgtcttg      240
cgtataaggg gaaagaacac cttggagaat gagcatgtta agataggaca attccatact      300
ctcgaacttg agcttcagcg accttttgtt ttaagaaaga aaatatggga ctcattggca      360
ttacatgttc tccggcaggc ctctgatcct ggtgcgagtg cagatctggc tgtggtacta      420
atgcaagaag ggctagcaaa tattttgctt gttggtaaaa gtatgacaag tacccgttca      480
cggattgaaa cttcaattcc tcgtaagcat ggacctgcca ttgctggtta tgaatcggct      540
ttgaagaagt tctttgagaa tgttctacag gctttcctca aacatgttga tttcaatgtt      600
gttcgctgtg ctgttattgc tagtcctggc ttcacaaagg accagttcca tcgtcatctt      660
atgttggagg cagaaagaag acaattgagg ccaattattg agaataagtc gcgaataatt      720
cttgtacata ctagctccgg atataagcat agtttgaaag aagtcttgga tgccccaaat      780
gttatgagca tgataaaaga caccaaagca gcgcaagagg tccgagctct caaggatttc      840
ttcaacatgc tttcaaatga tccggcacgt gcatgctacg gaccaaaaca tgtggaggtt      900
gcccatgagc gaatggcagt tcaaacactt cttattaccg acgatctctt caggaattcg      960
gatgtaatta cgaggcaaaa gtatgtcggt ttggtgaact ctgttaagaa ttcggggggc     1020
actgctcaca tttttttcgtc tatgcacgta tcaggggaac aactggcaca gctgaccggc     1080
attgcggcaa tccttcgttt ccctcttccg gatctggaag acatcgaaat gtag           1134
```

```
<210> SEQ ID NO 23
```

```
<211> LENGTH: 1140
<212> TYPE: DNA
<213> ORGANISM: Glycine max

<400> SEQUENCE: 23
atgaagatcg ttcggaaaga cctcgtaccc aatggacctg gcagcgttaa gatggttgca      60
gtggattcgg atgatctctg gtttgcgtat aacctgatag ctcccggaga ctctgtcatg     120
gccgttactg tcaggaaggt tctaagagaa gctgctagtg gcggacggga agcagaacgc     180
gtcaagctca aattggaaat taaagtccaa gagcttgctg attatgacaa agaaggttct     240
attttacgtg ttcgcggaaa gaacattttg gagaatgaat atgtcaagat aggagctttt     300
catactttag aactcgaact gcagcgcccg tttgtgctca gaaaggatgt ttgggattct     360
ttggctttgg aggtactaca gcaggcctct gatcctggtg caagtgctga tctagccgtg     420
gtgttgatgc aagaaggatt agcccatatc ctccttgttg gtagaagtat gactgttact     480
cgttcgcgga tagaaacatc aattcctcgc aaacatgggc ctgcaattgc tggttatgag     540
aaagctttgg ataagttctt tcagaatgtt ttgcaggctt tcttgaaaca tatagatttc     600
aacgtggttc gttgtgctgt aattgcaagt ccaggattta caaaggatca gtttcaccgt     660
cacttatttt tggaggcaga acgaagacag ttgcgaccta ttattgaaaa taaatcacgc     720
atcattcttg tgcatacaag ttcaggatac aaacatagct taaaggaggt tttggatgct     780
ccaaatgtca tgagtttaat aaaagatact aaagcagcac aagaggttcg agttatgaag     840
gatttctacg acatgctttc aaatgatcca tcacgtgctt gttatggaat gaaacatgtt     900
gaggttgcca atgaacgact agctgtacaa acgcttctca ttacggatga cttttcagg     960 aattcagata tagcaacaag aaaaaagtat gttaacttgg tcaactctgt taaggattca    1020
ggaggctctg tccatgtatt ttcgtccatg catgtctctg gagaacaact agcccagata    1080
agtggcattg ctgcaattct tcgatttcct ctccctgatc ttgaagacat tgagatgtga    1140

<210> SEQ ID NO 24
<211> LENGTH: 1140
<212> TYPE: DNA
<213> ORGANISM: glycine max

<400> SEQUENCE: 24
atgaagatcg ttcggagaga cctagtacct aatggacctg gcagcgttaa gatggtggca      60
gtggattcgg atgatctctg gtttgcgtat aacttgatag ctcccggaga ctctgtcatg     120
gccgttactg tcaggaaggt tctaagagaa gctgctaatg gcggacggga agcagaacgc     180
gtcaagctca aattggaaat taaagtcgaa gagctttctg attatgacaa agaaggttct     240
attttgcgtg ttcgtggaaa gaacattttg gagaatgaat atgtcaagat tggagcattt     300
catactttag aactcgaact gcagcggccg tttgtgctca gaaaggatgt ttgggattct     360
ttggctttgg aggtactaca gcaggcctcc gatcctggtg caagtgctga tctagcagtg     420
gtgttgatgc aagaaggatt agcccatatc ctccttgttg gtagaagtat gactgttact     480
cgttcgcgga tagaaacatc aattcctcgc aaacatgggc ctgcaattgc tggttatgag     540
aaagctttgg ataagttctt tcagaatgtt ttgcaggctt tcttgaaaca tatagatttc     600
aatgtggttc gttgtgctgt aattgcaagt ccaggattta caaaggatca gtttcaccgt     660
cacttatttt tggaagcaga acgaagacag ttgcgaccta ttattgaaaa caaatcccgc     720
atcattcttg tgcatacaag ttcaggatat aagcatagtt taaaggaggt tttggatgct     780
ccaaatgtca tgagtttgat aaaagatact aaagcagcac aagaggttcg agttatgaag     840
```

-continued

```
gatttctacg acatgctttc aaatgatcca tcacgtgctt gttatggaat gaaacatgtt      900
gaggttgcca atgaacgact agctgtacaa atgcttctca ttacggatga gcttttcagg      960
aattcagata tagcaacaag aaaaaagtat gttaacttgg tcaactctgt taaggattca     1020
gggggctctg tccatgtatt ttcgtccatg catgtctctg gagaacaact agcccagata     1080
agtggcattg ctgcgattct tcggtttcct ctccctgatc ttgaagacat tgagatgtga     1140
```

```
<210> SEQ ID NO 25
<211> LENGTH: 1137
<212> TYPE: DNA
<213> ORGANISM: Arabidopsis thaliana

<400> SEQUENCE: 25
atgaagatcg ttcgcaggga tttttgttcgt aatggacccg gaagcgttaa gatggtggca       60
gaggactctg atgatctctg gtatgcttat aacttgattg ctgtgggcga tagtgtaatg      120
gctgtcactt tcagaaaagt tcagagagag atacctggtg ggggaagaga ctctgaacgt      180
gttaaactga agctggaagt acaagttgag gaggtggact atgacaaaga cggatctgtt      240
ttgcgcatac gtggcaaaaa tatcctggag aatgagcacg taaagattgg tgcattccat      300
actttggaac ttgagctgaa acgaccttt gtgttgagaa aggaaatgtg ggactcaatg      360
gctcttgata cactcaaaca ggcctcagat cccgctgcta gtgctgatct agctgtagtt      420
ctaatgcaag aaggactggc acaaatcttc cttgtgggca gaagtgtgac aagtagccgt      480
gcacgaatag aaacatccat tcctaggaag catggacctg caattgctgg ttacgagtct      540
gctttgaaga aattttttga gaatgttctg caggcctttg tgaaacatgt tgacttcagt      600
gtcgttcgct gtgcagtagt tgcaagtccc ggcttcacaa aggatcagtt tcatcgccac      660
ttattgttgg aagcagaaag aagacaactg agacctatta ttgagaataa atcacgtata      720
atattggtgc acacaaactc tggatataga catagcctgg gtgaggttct ccatgccccc      780
aacgtgatga atatgataaa agatacaaaa gcagcaaaag aggtcaaagc tctcaatgat      840
tttcacaaca tgctttcaac tgaaccagat cgggcatgct atggaccaaa acacgtggaa      900
gttgcaaatg aacgaatggc aattcaaacg cttctcataa cggacgagct tttcaggaat      960
tctgacgtga aaacaaggaa gaagtatgtg aatttggtgg agtcggtaaa agattcggga     1020
ggagatgctt ttatattttc ggcgatgcat gtgtcaggag aacaattggc acagctgact     1080
ggaatagcag ctcttctcag gttcccttta ccagaactcg aagacattga gatgtaa        1137
```

```
<210> SEQ ID NO 26
<211> LENGTH: 1137
<212> TYPE: DNA
<213> ORGANISM: Solanum lycopersicum

<400> SEQUENCE: 26
atgaagattg ttcgtagaga ctttgttcct gatggttctg gtagtgtaaa gataattcca       60
gaagaagctg atgatctatg ggttgcttat aatctgatag ctgaaggtga tactgtatta      120
gctgttactg ttaggaaggt cctgagggaa gctgcttctg gaggaagaga tgctgaacga      180
gtgaaactga aattggaaat taaagttgag aatgtggagt atgacaaaga aggttctgcc      240
ttgcgtattc gcgggaagaa tattctggag aatgaacatg taaagatagg ggcctttcac      300
actctggaaa ttgagcaaca cagacctttt gtgctaagaa aggtggtctg ggactcactg      360
gcacgggagg ttcttcgtca agcttctgat ccatctgcaa gtgctgatct ggctgtggtt      420
```

-continued

```
ctgatgcaag aaggattggc acacattctt cttattggta aaagtgtgac tatcacccgt    480
tctcgtatag agtcttctat accgcgcaag catggaccgg ctattgcagg ttatgataag    540
gcgttaaata aattctttga caatgttcta caggcctttg tcaagcatgt tgatttcaaa    600
gtagttcgct gtgctgtgat tgcaagtcca ggattcacca aggatcagtt tcatcgtcac    660
ctgttgttgg aagccgagag gaagcaacta agacctataa tagaaaataa gtcacgcata    720
attcttgtcc atacaacctc gggatacaaa catagtttga aagaggttat ggatgcccca    780
aatgtaatga ctatgataaa agatacaaaa gctgccaaag aggttcaagc cctaaaggat    840
tttttcaaca tgctttcaaa tgatcctgat cgtgcatgct atggaccaaa gcatgttgaa    900
gttgcccatg agcgtctggc tattcagaca cttctcatta ctgacgagct ctttaggagt    960
tctgatgtag aaacgaggaa aaagtatgct aatttggtcg attcagtcaa ggattccaggt  1020 ggtactgctc tcattttctc gtcaatgcat gtctccggag aacaattgaa tcagctaacc   1080
ggcattgctg caatccttcg ttttcctttg ccggagctgg aagacattga gatgtga      1137
```

```
<210> SEQ ID NO 27
<211> LENGTH: 21
<212> TYPE: DNA
<213> ORGANISM: Capsicum annuum

<400> SEQUENCE: 27
tagaatattg agtatgacaa a                                                21

<210> SEQ ID NO 28
<211> LENGTH: 21
<212> TYPE: DNA
<213> ORGANISM: Artificial Sequence
<220> FEATURE:
<223> OTHER INFORMATION: Modified sequence of Capsicum annuum resulting
      in alternative splicing associated with exon 4

<400> SEQUENCE: 28
taaaatattg agtatgacaa a                                                21
```